US009567396B2

(12) United States Patent
Aikawa et al.

(10) Patent No.: US 9,567,396 B2
(45) Date of Patent: Feb. 14, 2017

(54) NOTCH INHIBITION IN THE PREVENTION OF VEIN GRAFT FAILURE

(71) Applicant: The Brigham and Women's Hospital, Inc., Boston, MA (US)

(72) Inventors: Masanori Aikawa, Chesnut Hill, MA (US); Toshiaki Nakano, Brookline, MA (US); Jun-ichiro Koga, Fukuoka (JP)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 14/855,380

(22) Filed: Sep. 16, 2015

(65) Prior Publication Data

US 2016/0002323 A1    Jan. 7, 2016

Related U.S. Application Data

(60) Continuation-in-part of application No. 13/903,288, filed on May 28, 2013, now Pat. No. 9,289,489, which is a continuation of application No. 13/358,425, filed on Jan. 25, 2012, now abandoned, which is a continuation of application No. 12/230,867, filed as application No. PCT/US2007/005267 on Mar. 2, 2007, now Pat. No. 8,133,857, application No. 14/855,380, which is a continuation-in-part of application No. 14/508,994, filed on Oct. 7, 2014, which is a division of application No. 13/461,365, filed on May 1, 2012, now Pat. No. 8,889,131, which is a continuation-in-part of application No. PCT/US2010/054798, filed on Oct. 29, 2010.

(60) Provisional application No. 60/779,445, filed on Mar. 7, 2006, provisional application No. 61/257,026, filed on Nov. 1, 2009.

(51) Int. Cl.
| | |
|---|---|
| A61K 39/395 | (2006.01) |
| A61K 31/7088 | (2006.01) |
| A61K 31/713 | (2006.01) |
| C07K 14/705 | (2006.01) |
| C07K 16/18 | (2006.01) |
| C12N 15/113 | (2010.01) |
| C07K 16/28 | (2006.01) |
| C07K 14/475 | (2006.01) |
| C07K 14/52 | (2006.01) |
| C07K 16/22 | (2006.01) |
| C07K 16/24 | (2006.01) |
| C12N 15/11 | (2006.01) |
| C12N 15/13 | (2006.01) |
| A61K 48/00 | (2006.01) |
| A61K 39/00 | (2006.01) |

(52) U.S. Cl.
CPC .......... *C07K 16/18* (2013.01); *A61K 31/7088* (2013.01); *A61K 31/713* (2013.01); *A61K 39/3955* (2013.01); *A61K 39/39533* (2013.01); *C07K 14/705* (2013.01); *C07K 16/28* (2013.01); *C12N 15/113* (2013.01); *A61K 39/395* (2013.01); *A61K 48/00* (2013.01); *A61K 2039/505* (2013.01); *C07K 16/22* (2013.01); *C07K 2316/96* (2013.01); *C07K 2317/76* (2013.01); *C12N 15/11* (2013.01); *C12N 15/1136* (2013.01); *C12N 2310/14* (2013.01)

(58) Field of Classification Search
CPC ..................... A61K 2039/505; A61K 39/3955; A61K 39/39558; A61K 39/39533; A61K 38/177; A61K 38/18; C07K 14/705; C07K 14/47; C07K 2316/96; C07K 2317/73; C07K 2317/76; C07K 16/18; C07K 16/22; C07K 16/28; C07K 2317/734; C07K 16/2863; C07K 16/2866

See application file for complete search history.

(56) References Cited

U.S. PATENT DOCUMENTS

| | | |
|---|---|---|
| 5,703,129 A | 12/1997 | Felsenstein et al. |
| 6,448,229 B2 | 9/2002 | Teall |
| 6,683,091 B2 | 1/2004 | Asberom et al. |
| 6,703,221 B1 | 3/2004 | Chan et al. |
| 6,756,511 B2 | 6/2004 | Castro Pineiro et al. |
| 6,890,956 B2 | 5/2005 | Churcher et al. |
| 6,967,196 B1 | 11/2005 | Smith et al. |
| 6,984,626 B2 | 1/2006 | Nadin et al. |
| 6,995,155 B2 | 2/2006 | Churcher et al. |
| 7,161,006 B2 | 1/2007 | Crawforth et al. |
| 7,183,303 B2 | 2/2007 | Castro Pineiro et al. |
| 7,365,196 B2 | 4/2008 | Belanger et al. |
| 7,906,116 B2 * | 3/2011 | Gill ...................... A61K 38/177 424/130.1 |
| 8,133,857 B2 | 3/2012 | Aikawa |
| 8,404,233 B2 | 3/2013 | Sunamura et al. |

(Continued)

FOREIGN PATENT DOCUMENTS

| | | |
|---|---|---|
| WO | WO 00/50391 A1 | 8/2000 |
| WO | WO 01/70677 A1 | 9/2001 |

(Continued)

OTHER PUBLICATIONS

Koga et al. Notch ligand delta-like 4 promotes vein graft disease: a novel mechanism. Atherosclerosis 126(21 Suppl): Abstract 16798, 2012.*

Shuhaiber et al. Mechanisms and future directions for prevention of vein graft failure in coronary bypass surgery. Eur J Cardio-thoracic Surg 22: 387-396, 2002.*

International Search Report for PCT/US2007/005267 filed Mar. 2, 2007.

Written Opinion of the International Searching Authority for PCT/US2007/005267 filed Mar. 2, 2007.

(Continued)

*Primary Examiner* — Bridget E Bunner
(74) *Attorney, Agent, or Firm* — Law Office of: Michael A. Sanzo, LLC

(57) ABSTRACT

The present invention is directed to methods of treating a patient to prevent vein graft failure by administering a compound that inhibits the Notch signaling pathway.

20 Claims, 18 Drawing Sheets

(56) References Cited

U.S. PATENT DOCUMENTS

| | | | |
|---|---|---|---|
| 8,889,131 | B2 | 11/2014 | Aikawa |
| 9,289,489 | B2 | 3/2016 | Aikawa |
| 2003/0180784 | A1 | 9/2003 | McCarthy et al. |
| 2004/0102390 | A1 | 5/2004 | Freier et al. |
| 2005/0025751 | A1 | 2/2005 | Bodmer et al. |
| 2005/0026831 | A1 | 2/2005 | Bodmer et al. |
| 2005/0075320 | A1 | 4/2005 | Nadin et al. |
| 2005/0143369 | A1 | 6/2005 | Castro Pineiro et al. |
| 2005/0227973 | A1 | 10/2005 | Brown et al. |
| 2005/0261276 | A1 | 11/2005 | Crawforth et al. |
| 2006/0004004 | A1 | 1/2006 | Asberom et al. |
| 2006/0009467 | A1 | 1/2006 | Josien et al. |
| 2006/0030694 | A1 | 2/2006 | Kitajewski et al. |
| 2006/0194315 | A1 | 8/2006 | Condie et al. |
| 2007/0213266 | A1 | 9/2007 | Gill et al. |
| 2007/0213329 | A1 | 9/2007 | Castro Pineiro et al. |
| 2008/0014196 | A1 | 1/2008 | Yan |
| 2008/0206753 | A1 | 8/2008 | Eagan et al. |
| 2009/0137470 | A1 | 5/2009 | Stylianou |
| 2009/0175849 | A1 | 7/2009 | Aikawa |
| 2009/0232813 | A1 | 9/2009 | Beauchamp et al. |
| 2010/0119526 | A1 | 5/2010 | Hellstrom |
| 2010/0303812 | A1 | 12/2010 | Sunamura et al. |
| 2011/0318339 | A1 | 12/2011 | Smider et al. |
| 2013/0064832 | A1 | 3/2013 | Aikawa |
| 2013/0336958 | A1 | 12/2013 | Aikawa |
| 2016/0130334 | A1 | 5/2016 | Aikawa et al. |

FOREIGN PATENT DOCUMENTS

| | | |
|---|---|---|
| WO | WO 02/081435 A1 | 10/2002 |
| WO | WO 03/012441 A1 | 2/2003 |
| WO | WO 03/018543 A1 | 3/2003 |
| WO | WO 03/041735 A3 | 5/2003 |
| WO | WO 03/042246 A2 | 5/2003 |
| WO | WO 2005/008250 A1 | 1/2005 |
| WO | WO 2007/103114 A2 | 9/2007 |
| WO | WO 2008/139202 A1 | 11/2008 |
| WO | WO 2009/025867 A2 | 2/2009 |
| WO | WO 2010/021729 A2 | 2/2010 |
| WO | WO 2010/054010 A1 | 5/2010 |

OTHER PUBLICATIONS

International Preliminary Report on Patentability for PCT/US2007/005267 filed Mar. 2, 2007.
International Search Report for PCT/US2010/054798 filed Oct. 29, 2010.
Written Opinion of the International Searching Authority for PCT/US2010/054798 filed Oct. 29, 2010.
International Preliminary Report on Patentability for PCT/US2010/054798 filed Oct. 29, 2010.
Supplementary European Search Report for counterpart European application EP 10 82 7551 prepared on Jun. 12, 2013.
Abedin, et al., "Vascular Calcification Mechanisms and Clinical Ramifications," *Arterioscler. Thromb. Vasc. Biol.* 24:1161-1170 (Jul. 2004).
Aikawa, et al., "The vulnerable atherosclerotic plaque Pathogenesis and therapeutic approach," *Cardiovasc. Pathol.* 13:125-138 (May-Jun. 2004).
Aikawa, et al., "Arterial and Aortic Valve Calcification Abolished by Elastolytic Cathepsin S Deficiency in Chronic Renal Disease," *Circulation* 119:1785-1794 (Mar. 2009).
Aikawa, et al., "Lipid Lowering by Diet Reduces Matrix Metalloproteinase Activity and Increases Collagen Content of Rabbit Atheroma: A Potential mechanism of Lesion Stabilization," *Circulation* 97:2433-2444 (Jun. 1998).
Aikawa, et al., "An HMG-CoA Reductase Inhibitor, Cerivastatin, Suppresses Growth of Macrophages Expressing Matrix Metalloproteinases and Tissue Factor In Vivo and in In vitro," *Circulation* 103:276-283 (Jan. 2001).

Aoyama, et al., "γ-Secretase inhibitor reduces diet-induced atherosclerosis in apolipoprotein E-deficient mice," *Biochem. Biophys. Res. Comm.* 383:216-221 (Apr. 2009).
Artavanis-Tsakonas, et al., "Notch Signaling: Cell Fate Control and Signal Integration in Development," *Science* 284:770-776 (Apr. 30, 1999).
Aster, et al., "Notch Signaling in Leukemia," *Annu. Rev. Pathol. Mech. Dis.* 3:587-613 (2008) (First published online as a Review in Advance on Oct. 17, 2007).
Bianchi, et al., "Physiology and Pathology of Notch Signalling System," *J. Cell. Physiol.* 207:300-308 (May 2006).
Bray, "Notch signalling: a simple pathway becomes complex," *Nat. Rev. Mol. Cell. Biol.* 7:678-689 (Sep. 2006).
Brou, et al., "A Novel Proteolytic Cleavage Involved in Notch Signaling: The Role of the Disintegrin-Metalloprotease TACE," *Mol. Cell* 5:207-216 (Feb. 2000).
Chawla, "Control of Macrophage Activation and Function by PPARs," *Circ. Res.* 106:1559-1569 (May 2010).
Chen, et al., "Rapid Discovery of Potent siRNA-Containing Lipid Nanoparticles Enabled by Controlled Microfluidic Formulation," *J. Am. Chem. Soc.* 134:6948-6951 (Apr. 2012).
Clément, et al., "Notch3 and IL-1 β exert opposing effects on a vascular smooth muscle cell inflammatory pathway in which NF-κB drives crosstalk," *J. Cell Sci.* 120:3352-3361 (Sep. 2007).
Coelho, et al., "Safety and Efficacy of RNAi Therapy for Transthyretin Amyloidosis," *N. Engl. J. Med.* 369:819-829 (Aug. 2013).
Conte, et al., "Results of Prevent III: A multicenter, randomized trial of edifoligide for the prevention of vein graft failure in lower extremity bypass surgery," *J. Vasc. Surg.* 43:742-751; discussion p. 751 (Apr. 2006).
Courties, et al., "In Vivo Silencing of the Transcription Factor IRF5 Reprograms the Macrophage Phenotype and Improves Infarct healing," *J. Am. Coll. Cardiol.* 63:1556-1566 (Apr. 2014).
Cox, et al., "Stranger in a Strange Land: The Pathogenesis of Saphenous Vein Graft Stenosis With Emphasis on Structural and Functional Differences Between Veins and Arteries," *Prog. Cardiovasc. Dis.* 34:45-68 (Aug. 1991).
Curry, et al., "Gamma secretase inhibitor blocks Notch activation and induces apoptosis in Kaposi's sarcoma tumor cells," *Oncogene* 24:6333-6344 (Jun. 2005).
Dahlman, et al., "In vivo endothelial siRNA delivery using polymeric nanoparticles with low molecular weight," *Nat. Nanotechnol.* 9:648-655 (Aug. 2014).
De Strooper, et al., "A Presenilin-1-Dependent γ-Secretase-Like Protease Mediates Release of Notch Intracellular Domain," *Nature* 398:518-522 (Apr. 8, 1999).
De Vries, et al., "Plaque Rupture Complications in Murine Atherosclerotic Vein Grafts Can Be Prevented by TIMP-1 Overexpression," *PLoS One* 7:e47134 (Oct. 2012).
Duncan, et al., "Integration of Notch and Wnt signaling in hematopoietic stem cell maintenance," *Nat. Immunol.* 6:314-322 (Mar. 2005).
Eckel, et al., "The Metabolic Syndrome," *Lancet* 365:1415-1428 (Apr. 2005).
Eefting, et al., "Local lentiviral short hairpin RNA silencing of CCR2 inhibits vein graft thickening in hypercholesterolemic apolipoprotein E3-Leiden mice," *J. Vasc. Surg.* 50:152-160 (Jul. 2009).
Esposito, et al., "The metabolic syndrome and inflammation: association or causation?" *Nutr. Metab. Cardiovasc. Dis.* 14:228-232 (Oct. 2004).
Evin, et al., "A Synthetic Substrate Assay for the Gamma-Secretase of the β-A4 Amyloid of Alzheimer's Disease," *J. Pept. Sci.* 1(2):132-139 (Mar./Apr. 1995).
Fitzgerald, et al., "Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial," *Lancet* 383:60-68 (Jan. 2014).
Fitzgibbon, et al., "Coronary Bypass Graft Fate and patient Outcome: Angiographic Follow-Up of 5,065 Grafts Related to Survival

(56) References Cited

OTHER PUBLICATIONS and Reoperation in 1,388 Patients During 25 Years," *J. Am. Coll. Cardiol.* 28:616-626 (Sep. 1996).
Fowkes, et al., "Comparison of global estimates of prevalence and risk factors for peripheral artery disease in 2000 and 2010: a systematic review and analysis," *Lancet* 382:1329-1340 (Oct. 2013).
Frank-Kamenetsky, et al., "Therapeutic RNAi targeting PCSK9 acutely lowers plasma cholesterol in rodents and LDL cholesterol in nonhuman primates," *PNAS* 105(33):11915-11920 (Aug. 2008).
Fukuda, et al., "Notch ligand Delta-like 1 blockade attenuates atherosclerosis and metabolic disorders," *Proc. Natl. Acad. Sci. USA* 109(27):E1868-1877 (Jul. 2012).
Fukushima, et al., "Notch ligand Delta-like4 inhibits the development of murine experimental allergic conjunctivitis," *Immunol. lett.* 121:140-147 (Dec. 2008).
Fung, et al., "Delta-Like 4 Induces Notch Signaling in Macrophages: Implications for Inflammation," *Circulation* 115:2948-2956 (May 2007).
Fung, et al., "Induction of the Pathway in Activated Human Macrophages," *Circulation* 110(17):274, Supplement III, Abstract 1312, (Oct. 26, 2004).
Gale, et al., "Haploinsufficiency of delta-like 4 ligand results in embryonic lethality due to major defects in arterial and vascular development," *Proc. Natl. Acad. Sci. USA* 101(45):15949-15954 (Nov. 9, 2004).
Garg, et al., "Mutations in NOTCH1 Cause Aortic Valve Disease," *Nature* 437:270-274 (Sep. 2005).
Goncharova, et al., "Assays for in vitro monitoring of human airway smooth muscle (ASM) and human pulmonary arterial vascular smooth muscle (VSM) cell migration," *Nat. Protoc.* 1(6):2933-2939 (Dec. 2006).
Hambleton, et al., "Structural and Functional Properties of the Human Notch-1 Binding Region," *Structure* 12:2173-2183 (Dec. 2004).
Hansson, et al., "Recording Notch Signaling in Real Time," *Dev. Neurosci.* 28:118-127 (Feb. 2006).
Hartley, et al., "Expression of infectious murine leukemia viruses by RAW264.7 cells, a potential complication for studies with a widely used mouse macrophage cell line," *Retrovirology* 5:1-6 (2008) (published online Jan. 4, 2008).
High, et al., "The multifaceted role of Notch in cardiac development and disease," *Nature Rev.* 9:49-61 (Jan. 2008).
Hofmann, et al., "Notch Signaling in Blood Vessels Who Is Talking to Whom About What?" *Circ. Res.* 100:1556-1568 (Jun. 2007).
Hoke, et al., "In Vitro Gama-Secretase Cleavage of the Alzheimer's Amyloid Precursor Protein Correlates to a Subset of Presenlin Complexes and Is Inhibited by Zinc," *FEBS J.* 272:5544-5557 (2005) (published online Oct. 6, 2005).
Holycross, et al., "Platelet-Derived Growth Factor-BB-Induced Suppression of Smooth Muscle Cell Differentiation," *Circ. Res.* 71:1525-1532 (Dec. 1992).
Hotamisligil, "Inflammation and metabolic disorders," *Nature* 444:860-867 (Dec. 2006).
Hsieh, et al., "Truncated mammalian Notch 1 Activates CBF1/RBPJk-Repressed Gense by a Mechanism Resembling That of Epstein-Barr Virus EBNA2," *Mol. Cell. Niol.* 16:952-959 (Mar. 1996).
Ikeuchi, et al., "The Notch Ligands, Delta1 and Jagged2, Are Substrates for Presenlin-Dependent "β-Secretase" Cleavage," *J. Biol. Chem.* 278(10):7751-7754 (Mar. 7, 2003).
Irabarren, et al., "Metabolic syndrome and early-onset coronary artery disease," *J. Am. Coll. Cardiol.* 48(9):1800-1807 (Nov. 2006).
Iso, et al., "Notch Signaling in Vascular Development," *Arterioscler. Thromb. Vasc. Biol.* 23:543-553 (2003) (published online Feb. 2003).
Itoh, et al., "Synergy and Antagonism Between Notch and BMP Receptor Signaling Pathways in Endothelial Cells," *EMBO J.* 23(3):541-551 (2004) (published online Jan. 2004).

Jiang, et al., "Interplay of CCR2 signaling and local shear force determines vein graft neointimal hyperplasia in vivo," *FEBS Lett.* 583:3536-3540 (Nov. 2009).
Kanasty, et al., "Delivery materials for siRNA therapeutics," *Nat. Mater.* 12:967-977 (Nov. 2013).
Kanda, et al., "MCP-1 contributes to macrophage infiltration into adipose tissue, insulin resistance and hepatic steatosis in obesity," *J. Clin. Invest.* 116(6):1494-1505 (Jun. 2006).
Kenagy, et al., "Proliferative capacity of vein graft smooth muscle cells and fibroblasts in vitro correlates with graft stenosis," *Vasc. Surg.* 49:1282-1288 (May 2009).
Koga, et al., "Macrophage Notch Signaling Accelerates Vein Graft Disease in Ldlr-/-Mice," Abstract 2.1, p. 21; International Society for Applied Cardiovascular Biology 14th Biennial Meeting (Apr. 2-5, 2014).
Koga, et al., "Macrophage Expression of the Notch Ligand Delta-Like 4 Promotes Vein Graft Disease in LDL Receptor-Deficient Mice," Abstract 11, p. 36; Arteriosclerosis, Thrombosis and Vascular Biology Scientific Sessions (May 1-3, 2014).
Koga, et al., "Essential Role of Angiotensin II Type 1a Receptors in the Host Vascular Wall, but Not the Bone Marrow, in the Pathogenesis of Angiotensin II-Induced Atherosclerosis," *Hypertens. Res.* 31:1791-1800 (Sep. 2008).
Koga, et al., "Soluble Flt-1 Gene Transfer Ameliorates Neointima Formation After Wire Injury in flt-1 Tyrosine Kinase-Deficient Mice," *Arterioscler. Thromb. Vasc. Biol.* 29:458-464 (Apr. 2009).
Leuschner, et al., "Therapeutic siRNA silencing in inflammatory monocytes in mice," *Nat. Biotechnol.* 29:1005-1010; (with online methods attached); (Nov. 2011).
Leuschner, et al., "Silencing of CCR2 in myocarditis," *Eur. Heart J.* 36:1478-1488 (Jun. 2014).
Li, et al., "Notch 3 signaling promotes the development of pulmonary arterial hypertension," *Nature Med.* 15(11):1289-1297 (Nov. 2009).
Liang, et al., "The Macrophage at the Crossroads of Insulin Resistance and Atherosclerosis," *Circ. Res.* 100:1546-1555 (Jun. 2007).
Libby, et al., "Stabilization of atherosclerotic plaques: New mechanisms and clinical targets," *Nat. med.* 8:1257-1262 (Nov. 2002).
Lindner, et al., "Members of the Jagged/Notch Gene Families Are Expressed in Injured Arteries and Regulate Cell Phenotype via Alterations in Cell Matrix and Cell-Cell Interaction," *Am. J. Pathol.* 159(3):875-883 (Sep. 2001).
Lobov, et al., "Delta-like ligang 4 (Dl14) is induced by VEGF as a negative regulator of angiogenic sprouting," *PNAS* 104:3219-3244 (Feb. 2007).
Love, et al., "Lipid-like materials for low-dose, in vivo gene silencing," *PNAS* 107(5):1864-1869; (1 page correction attached) (Feb. 2010).
Luscher, et al., "Vascular biology of coronary bypass grafts," *Curr. Opin. Cardiol.* 6:868-876 (Dec. 1991).
Malik, et al., "Impact of the metabolic syndrome on mortality from coronary heart disease, and all causes in United States adults," *Circulation* 110:1245-1250 (Sep. 2004).
Moore, et al., "Macrophages in atherosclerosis: a dynamic balance," *Nat. Rev. immunol.* 13:709-721 (Oct. 2013).
Moriyama, et al., "Delta-like 1 is essential for the maintenance of marginal zone B cells in normal mice but not in autoimmune mice," *Int. Immunol.* 20:763-773(Apr. 2008).
Motwani, et al., "Aortocoronary Saphenous Vein Graft Disease Pathogenesis, Predisposition, and prevention," *Circulation* 97:916-931 (Mar. 1998).
Mumm, et al., "A Ligand-Induced Extracellular Cleavage Regulates γ-Secretase-Like Proteolytic Activation of Notch1," *Mol. Cell* 5:197-206 (Feb. 2000).
Nobta, et al., "Critical Regulation of Bone Morphogenetic Protein-Induced Osteoblastic Differentiation by Delta1/Jagged1-Activated Notch1 Signaling," *J. Biol. Chem.* 280(16):15842-15848 (Apr. 22, 2005).
Novobrantseva, et al., "Systemic RNAi-mediated Gene Silencing in Nonhuman Primate and Rodent Myeloid Cells," *Mol. Ther. Nucleic Acids* 1 e4:1-13 (Jan. 2012).

(56) References Cited

OTHER PUBLICATIONS

Oishi, et al., "Blockade of Delta-Like Ligand 4 Signaling Inhibits Both Growth and Angiogenesis of Pancreatic Cancer," *Pancreas* 39:897-903 (Aug. 2010).

Ohtsuka, et al., "Visualzation of embryonic neural stem cells using Hes promoters in transgenic mice," *Mol. Cell. Neurosci.* 31:109-122 (Jan. 2006).

Owens, et al., "Elevated C-reactive protein levels are associated with postoperative events in patients undergoing lower extremity vein bypass surgery," *J. Vasc. Surg.* 45:2-9; discussion p. 9; (Jan. 2007).

Owens, et al., "Lower extremity vein graft failure: a translational approach," *Vasc. Med.* 13:63-74 (Feb. 2008).

Peri, et al., "Development of Human Protein Reference Database as an Initial Platform for Approaching Systems Biology in Humans," *Genome Res.* 13(10):2363-2371 (Oct. 2003).

Phillips, "The challenge of gene therapy and DNA delivery," *J. Pharm. Pharmacol.* 53:1169-1174 (Sep. 2001).

Pinnix, et al., "A Novel γ-Secretase Assay Based on Detection of the Putative C-Terminal Fragment-γ of Amyloid β Protein Precursor," *J. Biol. Chem.* 276(1):481-487 (Jan. 5, 2001).

Pirollo, et al., "Targeted delivery of small interfering RNA: approaching effective cancer therapies," *Cancer Res* 68(5):1247-1250 (Mar. 2008).

Poulos, et al., "Cell line models for differentiation: predipocytes and adipocytes," *Exp. Biol. Med.* 235:1185-1193 (published online Sep. 2010).

Qiao, et al., "The severity of atherosclerosis at sites of plaque rupture with occlusive thrombosis in saphenous vein coronary artery bypass grafts," *Am. Heart J.* 122:955-958 (Oct. 1991).

Quillard, et al., "Selective Inhibition of Matrix Metalloproteinase-13 Increases Collagen Content of Established Mouse Atherosclerosis," *Atheriosler. Thromb. Vasc. Biol.* 31:2464-2472; (with supplemental materials attached); (Nov. 2011).

Radtke, et al., "Notch Signaling in the Immune System," *Immunity* 32:14-27 (Jan. 2010).

Ridgeway, et al., "Inhibition of Dll4 signalling inhibits tumour growth by deregulating angiogenesis," *Nature* 444:1083-1087 (Dec. 2006).

Ridker, et al., "Effects of Interleukin-1 β Inhibition With Canakinumab on Hemoglobin A1c, Lipids, C-Reactive Protein, Interleukin-6, and Fibrinogen," *Circulation* 126:2739-2748 (Dec. 2012).

Robbins, et al., "Local proliferation dominates lesional macrophage accumulation in atherosclerosis," *Nat. Med.* 19:1166-1172; (with online methods attached); (Sep. 2013).

Rosenfeld, et al., "Macrophage and Smooth Muscle Cell Proliferation in Atherosclerotic Lesions of WHHL and Comparably Hypercholesterolemic Fat-fed Rabbits," *Atheriosclerosis* 10:680-687 (Sep. 1990).

Rubanyi, et al., "The future of human gene therapy," *Mol Aspects Med* 22:113-142 (Jun. 2001).

Rusanescu, et al., "Notch signaling in cardiovascular disease and calcification," *Curr Cardiol Rev* 4:148-156 (Aug. 2008).

Selkoe, et al., "Notch and Presenlin: Regulated Intrmembrane Proteolysis Links Development and Degenration," *Annu. Rev. Neurosci.* 26:565-597 (2003) (First published online as a Review in Advance on Apr. 18, 2003).

Sernee, et al., "Selecting Cells with Different Alsheimer's Disease γ-Secretase Activity Using FACS," *Eur. J. Biochem.* 270:495-506 (published online Jan. 2003).

Shi, et al., "Deficiency of the Cysteine Protease Cathepsin S Impairs Microvessel Growth," *Circ. Res.* 92:493-500 (Mar. 2003).

Shimizu, et al., "Physical Interaction of Delta1, Jagged1, and Jagged2 with Notch1 and Notch3 Receptors," *Biochem. Biophys. Res. Commun.* 276:385-389 (Sep. 2000).

Shimizu, et al., "Mouse Jagged1 Physically Interacts with Notch2 and Other Notch Receptors," *J. Biol. Chem.* 274(46):32961-32969 (Nov. 12, 1999).

Shimizu, et al., "Notch Signaling Induces Osteogenic Differentiation and Mineralization of Vascular Smooth Muscle Cells," *Arterioscler. Thromb. Vasc. Biol.* 29:1104-1111 (published online Apr. 2009).

Shimizu, et al., "CC Chemokine Receptor-1 Activates Intimal Smooth Muscle-Like Cells in Graft Arterial Disease," *Circulation* 120:1800-1813 (Nov. 2009).

Shimokama, et al , "Immunohistochemical and Ultrastructural Demonstration of the Lymphocyte-Macrophage Interaction in Human Aortic," *Mod. pathol.*4(1):101-107 (Jan. 1991).

Shutter, et al., "Dll4, a novel Notch ligand expressed in aterial endothelium," *Genes & Development* 14:1313-1318 (Jun. 2000).

Souihol, et al., "NAS Transgenic Mouse Line Allows Visualization of Notch Pathway Activity in Vivo," *Genesis* 44:277-286 (Jun. 2006).

Stockhausen, et al., "Effects of the Histone Deacetylase Inhibitor Valproic Acid on Notch Signaling in Human Neuroblastoma Cells," *Br. J. Cancer* 92:751-759 (Published online Feb. 1, 2005).

Subramanian, et al., "Dietary cholesterol worsens adipose tissue macrophage accumulation and atherosclerosis in obese LDL receptor-deficient mice," *Atherioscler Thromb Vasc Biol* 28:685-691 (Apr. 2008).

Sukhova, et al., "Expression of the Elastolytic Cathepsins S and K in Human Atheroma and Regulation of their Production in Smooth Muscle Cells," *J. Clin. Invest.* 102:576-583 (Aug. 1998).

Sutherland, et al., "The metabolic syndrome and inflammation," *Metabolic Syndrome and Related Disorders* 2(2):82-104 (Jun. 2004).

Swirski, et al.,"Ly-6C$^{hi}$ monocytes dominate hypercholesterolemia-associated monocytosis and give rise to macrophages in atheromata," *J. Clin. Invest.* 117(1):195-205 (Jan. 2007).

Takeda, et al., "Macrophage skewing by PHd2 haplodeficiency prevents ischaemia by inducing arteriogenesis," *Nature* 479:122-126; (with supplemental methods attached); (Nov. 2011).

Takizawa, et al., "Enhanced Gene Activation by Notch and BMP Signaling Cross-Talk," *Nucleic Acids Res.* 31(19):5723-5731 (Oct. 2003).

Tatewaki, et al., "Blockade of monocyte chemoattractant protein-1 by adenoviral gene transfer inhibits experimental vein graft neointimal formation," *J. Vsc. Surg.* 45:1236-1243 (Jun. 2007).

Thurston, et al., "The Delta paradox: DLL4 blockade leads to more tumor vessels but less tumour growth," *Nat. Rev. Cancer* 7:327-331 (May 2007).

Towler, et al., "Oxidation, Inflammation, and Aortic Valve Calcification," *J. Am. Coll. Cardiol.* 52(10):851-854 (Sep. 2008).

Twine, et al., "Graft type for femoro-popliteal bypass surgery (Review)," *Cochrane Database Syst. Rev.* 5:1-85 (Jan. 2010).

Van Der Wal, et al., "Specialized Membrane Contacts Between Immunocompetent Cells in Human Atherosclerotic Plaques," *Cardiovasc. Pathol.* 3:81-85 (Apr.-Jun. 1994).

Van Es, et al., "Notch/γ-Secretase Inhibition Turns Proliferative Cells in Intestinal Crypts and Adenomas into Goblet Cells," *Nature* 435:959-963 (Jun. 2005).

Wang, et al., "µ Opiate Receptor: cDNA Cloning and Expression," *Proc. Natl. Acad. Sci. USA*90:10230-10234 (Nov. 1993).

Weng, et al., "Activating Mutations of NOTCH1 in Human T Cell Acute Lymphoblastic Leukemia," *Science* 306:269-271 (Oct. 8, 2004).

Whitehead, et al., "Silencing or Stimulation? siRNA Delivery and the Immune System," *Annu. Rev. Chem. Biomol. Eng.* 2:77-96 (Feb. 2011).

Williams, et al., "Up-regulation of the Notch ligand Delta-like 4 inhibits VEGF-induced endothelial cell function," *Blood* 107(3):931-939 (Feb. 1, 2006).

Xu, et al., "Gamma-Secretase: Characterization and Implication for Alzheimer Disease Therapy," *Neurobiol. Aging* 23(6):1023-1030 (Nov./Dec. 2002).

Yamanda, et al., "Role of ephrinB2 in nonproductive angiogenesis induced by Delta-like 4 blockade," *Blood* 113:3631-3639 (Apr. 2009).

Yu, et al., "Lack of interleukin-1 signaling results in perturbed early vein graft wall adaptations," *Surgery* 153:63-69 (Jan. 2013).

(56) References Cited

OTHER PUBLICATIONS

Yu, et al., "Rationale and practical techniques for mouse models of early vein graft adaptations," *J. Vasc. Surg.* 52:444-452 (Aug. 2010).
U.S. Appl. No. 14/508,994, filed Oct. 7, 2014, Aikawa.
"Defining Adult Overweight and Obesity", www.cdc.gov/obesity/adult/defining.html, Jun. 16, 2014.
Chalk, M.B., "Obesity: Addressing a multifactorial disease," *The Case Manage* 15(6):47-49 (Nov./Dec. 2004).
Palou, et al., "Obesity: molecular bases of a multifactorial problem," *Eur. J. Nutr.* 39:127-144 (Jun. 2000).
Office Action for copending U.S. Appl. No. 14/508,994 mailed Jun. 24, 2016.
Koga, et al., "Macrophage Notch Ligand Delta-Like 4 Promotes Vein Graft Lesion Development, Implications for the Treatment of Vein Graft Failure," *Arterioscler. Thromb. Vasc. Biol.* 35:2343-2353 (Nov. 2015).

\* cited by examiner

NOTCH INHIBITION IN THE PREVENTION OF VEIN GRAFT FAILURE

CROSS REFERENCE TO RELATED APPLICATIONS

The present application is a continuation in part of U.S. Ser. No. 13/903,288, filed May 28, 2013, (now U.S. Pat. No. 9,289,489), which is a continuation of U.S. Ser. No. 13/358,425, filed on Jan. 25, 2012 (now abandoned). U.S. Ser. No. 13/358,425 is a continuation of U.S. Ser. No. 12/230,867, which has a US filing date of Mar. 2, 2007 (now U.S. Pat. No. 8,133,857) and which is US national stage of international application PCT/US2007/005267 (now expired). The '267 PCT application was filed internationally on Mar. 2, 2007 and claims the benefit of U.S. provisional application 60/779,445 filed on Mar. 7, 2006.

The present application is also a continuation in part of U.S. Ser. No. 14/508,994, filed on Oct. 7, 2014, which is a division of U.S. Ser. No. 13/461,365, filed on May 1, 2012 (now U.S. Pat. No. 8,889,131). U.S. Ser. No. 13/461,365 is a continuation in part of PCT/US2010/054798, filed on Oct. 29, 2010, (now expired), which claims the benefit of U.S. 61/257,026, filed on Nov. 1, 2009.

The foregoing applications are all incorporated by reference herein in their entirety, to the same extent as if each individual application was specifically and individually indicated to be incorporated by reference herein in its entirety.

STATEMENT OF GOVERNMENT FUNDING

The United States Government has a paid-up license in this invention and the right in limited circumstances to require the patent owner to license others under reasonable terms as provided for by the terms of an NIH Grant No. R01HL107550 awarded by the Department of Health and Human Services.

FIELD OF THE INVENTION

The present invention is in the field of methods of treating patients to prevent vein graft failure. This may be accomplished by administering a compound that inhibits the Notch signaling pathway in macrophages.

BACKGROUND OF THE INVENTION

The Notch Signaling Pathway

The Notch signaling pathway has been identified as playing an important role in many diverse biological functions, including differentiation, and cellular proliferation (see U.S. Pat. No. 6,703,221). This pathway is activated by four different transmembrane receptor subtypes (designated as Notch1-Notch4) that rely on regulated proteolysis. Expression patterns and functions of Notch depend on cell type and context. Following ligand binding, the receptor undergoes sequential cleavage by metalloproteases of the ADAM family (Bru, et al., *Mol. Cell* 5:207-216 (2000); Mumm, et al., *Mol. Cell* 5:197-206 (2000)) and the presenilin-dependent gamma-secretase (Selkoe, et al., *Annu. Rev. Neurosci.* 26:565-97 (2003); De Strooper, et al., *Nature* 398:518-522 (1999)). The final proteolytic cleavage step permits the intracellular domain of the Notch receptor to translocate to the cell nucleus where it interacts with transcription factors to induce target gene expression.

In the cell nucleus, the Notch intracellular domain undergoes ubiquitilation. Proteolytic processing of the Notch precursor protein by furin-protease and its trafficking to the cell membrane also determine turnover and availability of receptors, and, in turn, activation of this signaling pathway. Altered glycosylation of the Notch extracellular domain by Fringe protein family members may also modify efficiency of ligand binding.

Notch Signaling and Macrophage Activation

The Notch pathway contributes to biological processes during development and to disease mechanisms in adults (Bray, et al., *Nat. Rev. Mol. Cell. Biol.* 7:678-689 (2006); Artavanis-Tsakonas, et al., *Science* 284:770-776 (1999)). Direct cell-to-cell contract via the binding of a ligand to a Notch receptor, both of which are expressed on the cell surface, triggers downstream responses (Thurston, et al., *Nat. Rev. Cancer* 7:327-331 (2007)). We previously demonstrated that Dll4-mediated Notch signaling promotes macrophage activation (Fung, et al., *Circulation* 115:2948-2956 (2007); Fukuda, et al., *Proc. Nat'l Acad. Sci. USA* 109: E1868-1877 (2012)). Clinical and preclinical evidence has established the causal role of macrophages in arterial atherosclerosis (Aikawa, et al., *Cardiovasc. Pathol.* 13:125-138 (2004); Moore, et al., *Nat. Rev. Immunol.* 13:709-721 (2013)). Failing vein grafts also tend to contain macrophages (Fowkes, et al., *Lancet* 382:1329-1340 (2013)) but their role in the disease progression remains unclear.

Vein Graft Failure

Vein graft failure is a global health burden with no effective medical solutions (Owens, et al., *Vasc. Med.* 13:63-74 (2008)). Due to the pandemic of atherosclerotic peripheral artery disease (PAD) and the growing prevalence of underlying metabolic disorders (Fowkes, et al., *Lancet* 382: 1329-1340 (2013)) the incidence of vein graft failure is rising. Although many mechanisms for arterial diseases have been established, the pathogenesis of vein graft failure remains incompletely understood. Autologous saphenous vein grafts (SVGs) are widely used for PAD because they remain patent longer than artificial conduits (Twine, et al., *Cochrane Database Syst. Rev.* CD001487 (2010)). Approximately 50% of lower extremity SVGs, however, become occluded or narrowed within a year (Conte, et al., *J. Vasc. Surg.* 43:742-751 (2006). When PAD grafts fail, the only available therapeutic options are devastating limb amputation or invasive and expensive angioplasty or surgical revascularization. Coronary artery SVGs also fail at high rates (Fitzgibbon, *J. Am. Coll. Cardiol.* 28:616-626 (1996)). Although current therapies such as statins can reduce the onset of complications of arterial diseases (e.g., myocardial infarction) (Libby, et al., *Nat. Med.* 8:1257-1262 (2002)), no effective medical solutions are available for vein graft failure.

SUMMARY OF THE INVENTION

The invention is directed to a method of treating a patient for vein graft disease and to prevent vein graft failure by administering a therapeutically effective amount of a compound that inhibits a Notch signaling pathway, i.e., that is a "Notch inhibitor," in macrophages. As used herein, the term "therapeutically effective amount" refers to a sufficient amount of a Notch inhibitor to prevent the onset, or retard the progression of vein graft disease (characterized by intimal hyperplasia and progressive occlusion of the vein). The term "inhibitor" refers to any agent capable of blocking Notch signaling. Mechanisms of action of such Notch inhibitors include, but are not limited to, inhibition of gamma-secretase and subsequent suppression of Notch receptor cleavage, inhibition of Notch trafficking to the cell membrane, suppression of expression or function of ligands and/or receptors, inhibition of ligand turnover, cleavage, and/or endocytosis, modification of Notch glycosylation, alteration of ubiquitilation of Notch components including the Notch intracellular domain, modification of expression and/or activity of co-factors or effectors (e.g., members of the MAML family, RBP-Jkappa/CBF-1), and alteration of differentiation/population of undifferentiated cells in bone marrow or circulating blood.

Preferred inhibitors are compounds that either reduce the expression of a ligand that binds to a Notch receptor, or that inhibit a ligand from binding to Notch receptors on macrophages. These ligands include Delta-like 1 (Dll1), Delta-like 3 (Dll3), Delta-like 4 (Dll4), Jagged1, and Jagged2. In instances where the binding of a ligand to Notch receptors suppresses the progression of vein graft disease, the development of activators may be preferred. This may particularly be the case with respect to the ligands Jagged1 and Jagged2. The most preferred Notch inhibitors act by inhibiting the activation of a Notch signaling pathway by Dll4 and are either antibodies that block the binding of Dll4 to a Notch receptor (especially receptors of the Notch1 or Notch3 receptor subtype) or RNA interfering agents that block the expression of Dll4 in macrophages.

Antibodies and other compounds inhibit Notch signaling may be administered to patients on a daily, weekly, or monthly basis at a dose of 0.01 to 500 mg/kg (or 1-100 mg/kg). Other dosages may also be used and can be determined using methods that are standard in the art, taking into account dosing regimens, the type of agent being administered and the clinical characteristics of the patient being treated.

Typically, the patient treated will have peripheral artery disease or have undergone coronary bypass surgery and will have been implanted with an autologous saphenous vein graft. Compounds may be administered orally as a capsule, tablet or pill or systemically by injection. They may also be administered locally by injection, by infusing a vein graft with a compound before implantation and/or by implanting, in close proximity to a vein graft, a gel or other matrix that slowly releases compound. In general, inhibitors will be administered as part of a pharmaceutical composition comprising the compound along with a pharmaceutically acceptable carrier.

Although not required, levels of expression, function, or activity of Notch components in a biological sample may be used to indicate whether vein graft disease is present or progressing. Thus, the invention includes methods of assessing vein graft disease by assaying a test biological sample derived from a patient for the number of macrophages and/or amount of a Notch component that is present in the patient (particularly at, or near, the site of implantation); comparing the results obtained with one or more control samples; and concluding that the patient is at increased risk of vein graft failure if the number of macrophages and/or the f the amount, function, or activity of the Notch component is higher in the test biological sample than in the control samples. Other, currently available clinical tests such as ultrasound imaging may also be used to monitor the patency of vein grafts and it should be recognized that Dll4 may be effectively used without any special testing at all.

The test biological sample may be blood, plasma, or serum. The Notch component tested for may be a Notch receptor or a Notch ligand, particularly a ligand selected from the group consisting of: Delta1 (or Delta-like 1/Dll1), Delta3 (or Delta-like 3/Dll3), Delta4 (or Delta-like 4/Dll4), Jagged1, and Jagged2. Control samples may be selected using methods well known in the art and might constitute, for example, blood, serum plasma etc. from individuals known to be free of cardiovascular disease or from the population in general.

Although the present invention is described primarily in terms of autologous or allogenic grafts, it applies to other types of grafts as well, including xenogeneic grafts, artificial (or synthetic grafts), tissue engineered grafts and to arteriovenous (AV) fistula failure. Unless otherwise indicated herein, it will be understood that the present methods can be applied to all of these types of grafts.

DETAILED DESCRIPTION OF THE INVENTION

A. Inhibitory Compounds

Figure 1:
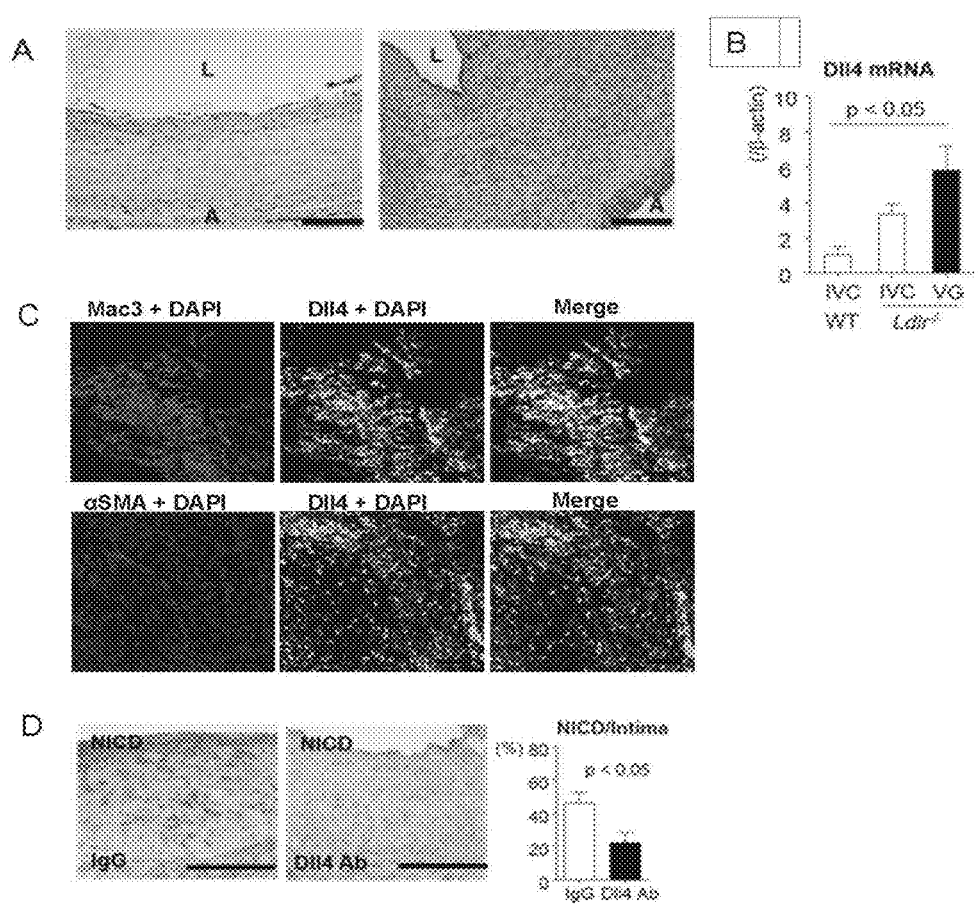
FIG. 1: Dll4 expression increases in human and mouse vein grafts. (A) Human SVG harvested for bypass surgery (control native vein, left) and failed SVG (right). Sections were stained with anti-Dll4 antibody. Scale bar indicates 300 µm. L, lumen; A, adventitia. The data represent 5 native veins and 5 failed vein grafts. Four other controls and failed grafts are shown in FIG. 8. (B) Dll4 mRNA in mouse vein grafts (VG) analyzed 28 days after grafting. Data are shown as relative expression normalized by native IVCs from wild type (WT) mice. n=5 to 8. (C) Dll4 expression in macrophages and smooth muscle cells in vein grafts of mice treated with control IgG or Dll4 blocking antibody for 28 days. Upper panels show double staining of Mac-3 and Dll4. Lower panels show double staining of α-SMA and Dll4. Arrows indicate double-positive cells. Scale bars indicate 100 µm. Each n=3 (D) Immunostaining of cleaved Notch1 intracellular domain (NICD) at 28 days after vein grafting. Scale bars indicate 100 µm. Bar graph shows quantification of Notch signal activation evaluated as a percentage NICD-positive area in intima. n=4

The present invention is directed to methods in which an inhibitor of Notch signaling is administered to a patient to prevent the onset or progression of vein graft disease and, ultimately, vein graft failure. Any of the Notch inhibitors discussed herein or elsewhere in the art may be used in these methods. References describing such inhibitors and the way in which they can be made, purified, and used include: U.S. Pat. No. 5,703,129; U.S. Pat. No. 6,448,229; U.S. Pat. No. 6,683,091; U.S. Pat. No. 6,756,511; U.S. Pat. No. 6,890,956; U.S. Pat. No. 6,984,626; U.S. Pat. No. 6,995,155; WO 01/70677; WO 02/081435; WO 03/018543; WO 00/50391; WO 03/0422646; WO 03/041735; U.S. published application 2005-0227973; 2006-0030694; 2006-0004004; 2006-0009467; 2005-0261276; 2005-0143369; and 2005-0075320, all of which are hereby incorporated by reference.

B. Drug Formulation

The compounds described above will typically be administered to patients in a pharmaceutical composition comprising the compound along with a pharmaceutically acceptable carrier. The carrier may be any solvent, diluent, liquid or solid vehicle that is pharmaceutically acceptable and typically used in formulating drugs. Guidance concerning the making of pharmaceutical formulations can be obtained from standard works in the art (see, e.g., *Remington's Pharmaceutical Sciences*, 16$^{th}$ edition, E.W. Martin, Easton, Pa. (1980)). In addition, pharmaceutical compositions may contain any of the excipients that are commonly used in the art. Examples of carriers or excipients that may be present include, but are not limited to, sugars (e.g., lactose, glucose and sucrose); starches, such as corn starch or potato starch; cellulose and its derivatives (e.g., sodium carboxymethyl cellulose, ethyl cellulose, or cellulose acetate); malt; gelatin; talc; cocoa butter; oils (e.g., peanut oil, cottonseed oil, safflower oil, sesame oil, olive oil, corn oil, or soybean oil); glycols; buffering agents; saline; Ringer's solution; alcohols; lubricants; coloring agents; dispersing agents; coating agents; flavoring agents; preservatives; or antioxidants.

The invention is compatible with the delivery of compounds by any route known in the art, including peroral, internal, rectal, nasal, lingual, transdermal, intravenous, intra-arterial, intramuscular, intraperitoneal, intracutaneous and subcutaneous routes. The most preferred route is oral, especially using dosage forms such as tablets, capsules or solutions. In cases where a compound is susceptible to degradation in the stomach of a patient, it may be enterically coated or it may be administered parenterally.

It will be understood that pharmaceutical compositions may contain any pharmaceutically acceptable form of an inhibitory compound, i.e., any form which maintains therapeutic activity and which does not cause unacceptable adverse effects when administered. For example, a compound may be in the form of a pharmaceutically acceptable salt, ester or pro-drug.

Liquid dosage forms for oral administration include, but are not limited to, pharmaceutically acceptable emulsions, microemulsions, solutions, suspensions, syrups and elixirs. In addition to the active compounds, liquid dosage form may contain inert diluents commonly used in the art, such as, for example, water, or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethyl formamide, oils, glycerol, alcohols, polyethylene glycols, and fatty acid esters.

Injectable preparations may be in the form of sterile, injectable aqueous or oleaginous suspensions, diluents or solvents that may be used may include 1,3-butanediol, water, Ringer's solution and isotonic saline solutions. In addition, oils or fatty acids may be present.

Pharmaceutical compositions will typically be given to a patient in one or more unit dosage forms. A "unit dosage form" refers to a single drug administration entity, e.g., a single tablet, capsule or injection vial. The amount of inhibitory compound present should be at least the amount required to reduce the development or progression of vein graft disease when one or more unit dosage forms are administered to a patient. On a biological level, sufficient inhibitor should be present to reduce the Notch signaling pathway in macrophages. Exact dosages given and amount of inhibitor in unit dosage forms may be determined for individual compounds using methods that are well known in the art of pharmacology and may be further adjusted by physicians on a case-by-case basis based on clinical considerations.

C. Treatment Methods

Subjects, particularly individuals at risk of vein graft failure may be treated by administering one or more of the inhibitory compounds described above. The exact dosage will depend upon the particular compound being given and will be determined using procedures well known in the art, balancing toxicity and therapeutic efficacy. Compounds may also be given to test animals to study their effect on vein graft disease. In these cases, dosages are limited only by toxicity. It should also be recognized that inhibitory compounds may be administered as the sole active agents in a dosage form, or they may be combined with other drugs to improve overall effectiveness.

D. Assays

Assays designed to identify compounds of potential use in the treatment or prevention of vein graft disease may involve any method known in the art for identifying compounds that block the Notch signaling pathway. The most common assays will be either enzymatic assays for inhibitors of gamma-secretase or assays to identify agents that interfere with receptor binding or ligand expression. In the former case, many different assays have been described in the art which may be utilized for examining the effect of a test compound on gamma-secretase activity. These include assays using radiolabeled substrates followed by HPLC or TLC analysis (see, e.g., Evin, et al., *J. Pept. Sci.* 1(2):132-139 (1995)); FACS assays (Sernee, et al., *Eur. J. Biochem.*

270:495-506 (2003)); and other in vitro or in vivo assays (Pinnix, et al., *J. Biol. Chem.* 276:481-487 (2001); Xu, et al., *Neurobiol. Aging* 23(6):1023-1030 (2002); and Holke, et al., *FEBS J.* 272:5544 (2005)). All of these references are hereby incorporated by reference in their entirety. Commercially available assays such as the QTL Lightspeed assay (QTL Biosystems, Santa Fe, N. Mex.) may also be used.

Receptor binding assays may be adapted to identify compounds that interfere with the binding of Notch ligands have been described in the art and may be used in conjunction with the present invention (see, e.g., Shimizu, et al., *J. Biol. Chem.* 274(46):32961-32969 (1999); Shimizu, et al., *Biochem. Biophys. Res. Commun.* 276(1):385-389 (2000), both of which are hereby incorporated by reference in their entirety). In general, receptor binding assays are performed using a source of Notch receptor together with one of the ligands that are known to bind to the receptor and with the compound being tested for binding activity. As a source of receptor, mammalian cells that have been transformed to recombinantly express Notch1-Notch4 may be used. The assay itself may be performed either with intact cells or with membranes prepared from the cells (see, e.g., Wang, et al., *Proc. Natl. Acad. Sci. USA* 90:10230-10234 (1993)). The membranes or cells are incubated with one of the ligands for the Notch receptor (e.g., Delta1 (Delta-like 1/Dll1), Delta4 (Delta-like 4/Dll4), Jagged 1 or Jagged 2) and with a preparation of the compound being tested. After binding is complete, the receptor is separated from the solution containing ligand and test compound, e.g., by filtration, and the amount of binding that has occurred is determined. Preferably, the ligand used is detectably labeled with a radioisotope such as $^{125}$I, however, fluorescent chemiluminescent or enzymatic labels can also be used. In a preferred embodiment, cell lines stably expressing one of the ligands (e.g., Dll4) and recombinant Notch1-4 may be used for binding assay.

Nonspecific binding may be determined by carrying out the binding reaction in the presence of a large excess of unlabeled ligand. For example, labeled ligand may be incubated with receptor and test compound in the presence of a thousand-fold excess of unlabeled ligand. Nonspecific binding should typically be subtracted from total binding, i.e., binding in the absence of unlabeled ligand, to arrive at the specific binding for each sample tested. Other steps, such as washing, stirring, shaking, filtering and the like may be included in the assays as necessary. Typically, wash steps are included after the separation of membrane-bound ligand from ligand remaining in solution and prior to quantitation of the amount of ligand bound, e.g., by counting radioactive isotope. The specific binding obtained in the presence of test compound is compared with that obtained in the presence of labeled ligand alone to determine the extent to which the test compound has displaced receptor binding.

In performing binding assays, care must be taken to avoid artifacts which may make it appear that a test compound is interacting with the Notch receptor when, in fact, binding is being inhibited by some other mechanism. For example, the compound being tested should be in a buffer which itself substantially inhibits the bind of ligand to the Notch receptor and should, preferably, be tested at several different concentrations. In addition, it is desirable that compounds identified as displacing the binding of ligand to receptor be reexamined in a concentration range sufficient to perform a Scatchard analysis of the results. This type of analysis is well known in the art and can be used for determining the affinity of a test compound for receptor (see, e.g., Ausubel, et al., *Curr. Protocols in Mol. Biol.*, 11.2.1-11.219 (1993); *Laboratory Techniques in Biochemistry and Molecular Biology*, Work, et al., NY (1978)). Computer programs may be used to help in the analysis of results (see, e.g., Munson, *Meth. Enzymol.* 92:543-577 (1983)).

The effects/actions of compounds can also be determined by other indicators of activated states of Notch signaling including, but not limited to, receptor cleavage and/or nuclear translocation, ligand cleavage and/or endocytosis, Notch trafficking to cell membrane, expression of ligands and/or receptors, ligand turnover, cleavage, and/or endocytosis, Notch glycosylation, ubiquitilation of Notch components including Notch intracellular domain, and expression and/or activity of co-factors or effectors (e.g., members of the MAML family, RBP-Jkappa/CBF-1), and differentiated state or population of undifferentiated cells in bone marrow or circulating blood.

E. Uses

The most obvious use of the present invention is in the administration of compounds to individuals to treat or prevent vein graft disease. It should be appreciated however that treatments may also involve administering compounds to test animals by scientists interested in studying the biology of vein graft disease and in finding new ways to prevent vein graft failure.

EXAMPLES

Example 1

Delta-Like 4 Induces Notch Signaling in Macrophages: Implications in Inflammation The Notch family members (Notch1-4) are large type I transmembrane receptors that undergo proteolytic processing by a furin-like convertase during transit to the cell surface (Logeat, et al., *Proc. Nat'l Acad. Sci. USA* 95:8108-8112 (1998)). Binding of a ligand—Delta-like 1 (Dll1), Delta-like 3 (Dll3), Delta-like 4 (Dll4), Jagged1, or Jagged2—triggers sequential receptor cleavage by ADAM-type metalloproteinases and gamma-secretase, resulting in the liberation and nuclear translocation of Notch intracellular domain (Notch$^{ICD}$) (Selkoe, et al. Annu. Rev. Neurosci. (2003)). Notch$^{ICD}$ association with the sequence-specific DNA-binding factor RBP-Jkappa/CBF-1 leads to the formation of a transcriptional activator complex that induces the transcription of Notch target genes. In the present example, data is presented showing that Dll4 expression increases in activated human macrophages, and that Dll4 binding induces pro-inflammatory responses. The findings suggest that the Dll4-Notch pathway participates in inflammatory states characterized by macrophage activation.

A. Methods

Cell Cultures

Human peripheral blood mononuclear cells were isolated by density gradient centrifugation and cultured in RPMI-1640 containing 5% human serum. In stimulation assays, confluent macrophages were treated with Ultra-pure LPS (InvivoGen), cytokines or minimally-modified LDL (mmLDL). Co-culture experiments employed a murine stromal cell line stably-transfected with a construct expressing human Dll4-GFP (MS5-Dll4) or GFP (MS5-GFP). Resuspended MS5 cells were overlain on human primary macrophages for the indicated duration, and rinsed thoroughly whereupon MS5 cells readily detached.

Reverse Transcription and Quantitative Polymerase Chain Reaction (qPCR)

TaqMan qPCR was performed on GeneAmp 5700 (Applied Biosystems). qPCR detection of human Dll4, Toll-like receptor 4 (TLR4), inducible nitric oxide synthase (iNOS), pentraxin 3 (PTX3) and Id1 was performed on iCycler (BioRad). qPCR values were GAPDH-normalized and relative fold changes calculated by comparative threshold cycles ($C_T$) method, $2^{-deltaCT}$.

Transfection and RBP-Jkappa/CBF-1 Luciferase Reporter Assay 200 nM of small interfering RNA (siRNA) was applied to human macrophages using cationic lipid-mediated transfection. RBP-Jkappa/CBF-1 firefly-luciferase reporter construct and pRL-TK-*Renilla* luciferase were co-transferred into RAW264.7 cells using electroporation. RAW264.7 cells were then co-cultured with MS5-Dll4 or MS5-GFP cells for 48 h. Luciferase activities were determined using the Dual-Luciferase Reporter Assay System (Promega).

Dll4.Fc Binding Assay

Dll4.Fc protein was generated using human full-length Dll4 cDNA subcloned into human IgG1 fusion protein vector, pEd.Fc. Dll4.Fc binding assays were performed using human macrophages. After blocking non-specific binding, 1 µg per reaction of Dll4.Fc or control Fc fragment pre-incubated with 0.5 µg biotinylated anti-human goat IgG at 15-20° C. was added for 30 min at 4° C. Streptavidin-PE (2.5 µg/ml) was then added for 45 min at 4° C.

Immunohistochemistry and Western Blotting

Immunohistochemistry employed fresh-frozen sections of discarded human carotid endarterectomy specimens, collected in accordance with a protocol approved by the IRB of the Brigham and Women's Hospital. For Western blotting, 80 µg of sample protein was loaded into each lane. Blots were stained with antibodies. Following incubation with HRP-tagged secondary antibodies, an ECL detection kit (Perkin Elmer) was used to reveal antibody binding.

Statistical Analysis

P values were obtained using the Mann-Whitney U test to compare GAPDH-normalized $C_T$ between control and treatment groups, or between day 0 and days 5, 7, or 10 samples. Individual relative fold changes were calculated using the equation $2^{-deltaCT}$ and expressed as mean relative fold changes±standard error of the mean (S.E.M.). Pearson's correlation coefficient (R) with two-tailed test of significance was used to determine bivariate correlations.

B. Results

Notch3 Increases During Monocyte-Macrophage Differentiation

To explore the possible role of the Notch pathway in macrophages, we used real-time RT-PCR to examine the expression of Notch pathway components during the differentiation of human monocytes to macrophages in culture. Differentiation was gauged by the expression levels of macrophage scavenger receptor A (SR-A), a macrophage marker. At day 10 in culture, macrophages (n=4) expressed mRNAs for multiple Notch receptors and ligands (mean PCR $C_T$: Notch1, 30.77; Notch2, 26.89; Notch3, 28.45; Notch4, 33.91; Dll1, 34.79; Dll3, 36.45; Dll4, 40.00; Jagged 1, 28.38; Jagged 2, 35.75). Notably, expression levels of Dll4 were lower than those of other Notch ligands. Macrophages also expressed ADAMs that participate in receptor cleavage, and Fringe proteins that modulate ligand-mediated signaling (mean PCR $C_T$: ADAM10, 25.31; ADAM17, 28.43; Lunatic Fringe, 33.87; Manic Fringe, 27.62; Radical Fringe, 26.59). Differentiation was accompanied by a marked rise in Notch3 mRNA, which increased 10.1±5.0 fold and 16.4±11.4 fold by days 7 and 10, respectively (both P<0.05). In contrast, Notch1 and Notch4 mRNA expression was reduced at days 7 and 10 (both P<0.05), whereas Notch2 expression was unchanged. Jagged2, Manic Fringe, and Radical Fringe also increased during macrophage differentiation. Western blots showed increased expression of full-length Notch3 protein at day 10, corroborating the mRNA findings. Relative to their intrinsic GAPDH expression, human primary macrophages expressed more Notch3 mRNA than human aortic SMC and radial artery EC (both P<0.05 vs. macrophages).

Proinflammatory Stimuli Induces Dll4 Expression in Human Macrophages

We used LPS (Ultra-pure LPS, InvivoGen) to broadly ascertain the effects of a proinflammatory stimulus on the Notch pathway in human primary macrophages. LPS stimulation (100 ng/ml) for 3 h led to a dramatic induction of Dll4 mRNA in 24 different macrophage donors (3,776.3±1717.1 fold increase, P=3.08×10⁻⁷). One donor among four represents Dll4 expression triggered by LPS in a time- and dose-dependent manner. The expression of Notch receptors did not change substantially with LPS treatment. LPS increased mRNA levels of Jagged1 (6.1±1.2 fold, P<0.01) and ADAM17 (3.0±0.7 fold, P<0.05, n=5).

We also examined the effects of other proinflammatory stimuli that are implicated in atherogenesis. mmLDL and IL-1beta increased Dll4 mRNA expression (68.7±36.3 fold and 130.9±61.7 fold, respectively, at 3 h, both P<0.01) in macrophages, whereas tumor necrosis factor alpha (TNF-alpha), interferon gamma (IFN-gamma) and granulocyte macrophage-colony stimulating factor (GM-CSF) had no significant effect.

Western blot analysis showed that LPS and IL-1beta also increased expression of Dll4 protein. Furthermore, although the mRNA and protein levels of Notch3 were not increased, in Western blots stained with an antibody specific for the intracellular domain of Notch3, we observed that LPS induced a shift in the Notch3 polypeptides from 280 kD (the size of newly synthesized, unprocessed Notch3) to 100 kD (the size of furin-processed Notch3). These findings suggest that LPS increases the furin-processing of Notch3, an event that is predicted to enhance both the surface expression of Notch3 and therefore its availability to ligand.

TLR4 Silencing and NF-kappaB Inhibition Limits Dll4 Induction by LPS

TLR4 serves as a receptor for LPS. TLR4 siRNA treatment silenced TLR4 mRNA expression in human macrophages (P<0.05 vs. control siRNA), and decreased LPS-induced Dll4 mRNA expression (P<0.05 vs. LPS+control siRNA). To examine the possible role of the NF-kappaB pathway downstream of TLR4 in LPS-induced Dll4 expression, we used a cell-permeable peptide, SN50 (Calbiochem), that inhibits nuclear translocation of the active NF-kappaB complex containing the p50 subunit. SN50 substantially reduced Dll4 expression at 100 µg/ml (95.8±3.3%; P<0.05 vs. LPS only group), whereas SN50M, the control peptide, did not affect Dll4 expression.

Dll4 Binding to Macrophages Triggers Notch Signaling

To examine whether Dll4 binds to macrophages and triggers Notch signaling, we performed four assays. First, we detected significant binding of the Dll4.Fc-biotinylated IgG complex to human macrophages as compared to the control Fc-biotinylated IgG complex or streptavidin-PE alone. Other experiments were conducted with feeder cell lines stably transfected with a vector expressing GFP alone (MS5-GFP) or Dll4-GFP (MS5-Dll4); these feeder cells are much less adherent to culture dishes than are macrophages, making it possible to remove these cells prior to harvesting of macrophages for analysis. Human primary macrophages co-cultured with MS5-Dll4 generated Notch1$^{ICD}$, the activated form of Notch1. The accumulation of Notch1$^{ICD}$ was sensitive to compound E, a potent gamma-secretase inhibitor, suggesting that Dll4 activates the canonical Notch signaling pathway. Third, the Dll4.Fc-IgG complex, but not Fc-IgG, also induced Notch1$^{ICD}$ production. Fourth, when co-cultured with MS5-Dll4 cells, the RAW264.7 macrophage cell line showed a >10-fold increase in the activity of a Notch-sensitive luciferase reporter gene that contains multiple binding sites for RBP-Jkappa/CBF-1, the key transcription factor that acts downstream of Notch.

Dll4-Notch Binding Induces Inflammatory Pathways and Genes in Macrophages

Of further interest, Dll4 binding increased phosphorylated extracellular signal-regulated kinases 1 and 2 (ERK1/ERK2) and Akt in human primary macrophages, indicating that Notch signaling induces mitogen-activated protein kinase (MAPK) and Akt pathways in this cell type. Co-culture with MS5-Dll4 also decreased IkappaBalpha accumulation in human primary macrophages, indicative of activation of the NF-kappaB pathway. Furthermore, Dll4-activated Notch signaling augmented inflammation-associated molecules including iNOS (n=12, p<0.01), PTX3 (n=12, p<0.01), and Id1 (n=5, p<0.01) in day 10 macrophages. siRNA targeting each of the four Notch receptors led to partial reduction of Dll4-induced increase of iNOS, PTX3 and Id1, suggesting functional signaling of Dll4 through all four Notch receptors. Additionally, Notch3 siRNA applied to day 5 differentiating macrophages led to diminished expression of iNOS, PTX3, Id1 and SR-A at day 10 when macrophages become differentiated. Dll4 binding further promoted macrophage expression of Dll4 (n=4, p<0.01), suggesting the positive Dll4-Notch feedback loop.

Dll4 Colocalizes with Macrophages in Human Atherosclerotic Plaques

Immunohistochemical staining for Dll4 and other Notch components, including Notch3, colocalized with immunoreactive CD68, a macrophage marker, in the tunica intima of human atherosclerotic plaques. Neither nonimmune IgG nor PBS showed positive staining. Computer-assisted color image quantification followed by statistical regression analysis demonstrated that immunoreactivity for Dll4 correlated positively with CD68 staining. Although immunostaining did not demonstrate clearly whether subpopulations of macrophages express Dll4, Notch3, or both, there was a strong statistically significant correlation between Dll4 and Notch3 staining. Staining for other ligands—Dll1, Jagged1, and Jagged2—also correlated positively with CD68 staining. Taken together, these data suggest that atherosclerotic plaques rich in macrophages contain greater amounts of Notch components.

C. Discussion

The present study affirms our hypothesis that the Notch pathway plays an important role in macrophages, a key cell type in inflammation and atherosclerosis. Evidence supporting this idea includes: 1) the expression of multiple Notch receptors and ligands in human macrophages; 2) markedly enhanced Dll4 expression in human macrophages stimulated with LPS, mmLDL, or IL-1beta, an event that likely involves TLR4 and NF-kappaB; 3) the ability of Dll4 to bind to macrophages and trigger Notch signaling; 4) Dll4-triggered activation of the MAPK, Akt, and NF-kappaB pathways in macrophages; 5) augmentation of gene transcription of iNOS, PTX3, Id1, and Dll4 through Dll4-induced Notch signaling; and 6) increased expression of Notch pathway components including Dll4 and Notch3 in human atherosclerotic plaques rich in macrophages. Taken together, our results concur with the hypothesis that Notch signaling participates in juxtacrine homotypic communication between macrophages and also in amplification of the proinflammatory milieu in inflamed tissues.

Example 2

Notch Signaling Induces Macrophage Gene Expression Associated with Inflammation and Atherosclerosis The present example presents results that demonstrate that Notch signaling regulates the induction of various proinflammatory genes, suggesting that this pathway participates in macrophage activation and the pathogenesis of inflammatory diseases including atherosclerosis.

A. Methods

Cell Culture

RAW 264.7 cells were from American Type Culture Collection (ATCC), and were grown at 37° C. under 5% CO2 in Dulbecco's modified Eagle's medium (DMEM, Gibco) supplemented with 10% fetal bovine serum (Bio-Whittaker), 4 mM L-glutamine, 50 U of penicillin G/ml, and 50 mg of streptomycin/ml.

Plasmid Construction and Purification

Plasmid DNA constructs encoding FLAG-tagged intracellular domains of mouse Notch1 (N1ICD), Notch2 (N2ICD), Notch3 (N3ICD), the dominant negative mastermind-like protein 1 (DNMAML1) and eGFP were amplified in chemically competent E. coli, purified using EndoFree Plasmid Kits (Qiagen), and resuspended in endotoxin free TE buffer with a concentration at 1.0 mg/ml for transfection.

Plasmid DNA Transfection

The cells were subcultured in a 150 cm$^2$ flask, three days before the transfection studies to reach about 80-90% confluency. Plasmid transfection employed electroporation. In each reaction, 4.0×10$^6$ RAW 264.7 cells were electroporated with plasmid DNA. The protein expression of N3ICD was confirmed by immunoblotting using anti-FLAG antibody (Sigma, St. Louis, Mo.). We also confirmed the N3ICD expression within 48 h after the transfection by following up the time course of mRNA expression by real-time PCR.

Luciferase Assay

We collected transfected cells 48 h after transfection and measured luciferase activity in a Berthold luminometer (Lumat LB9501, Berthold Technology) using the dual luciferase reporter assay system (Dual-Luciferase Reporter Assay System, Promega). The efficiency of transcription was measured and normalized in relation to the activity of pRL-SV40 *Renilla* (Promega), and the activity reported as the ratio of firefly/*Renilla* luciferase activity according to the manufacture's instruction.

DNA Microarray Analysis

We employed a high-throughput DNA microarray (Affymetrix GeneChip Mouse Genome 430A 2.0 Array (Affymetrix) representing approximately 14,000 well-characterized mouse genes) on total RNA samples obtained from N3ICD-transfected (n=3) or vehicle-transfected (n=3) RAW 264.7 cells at the GeneChip Microarray Facility of Harvard Medical School-Partners Healthcare Center for Genetics and Genomics. In each reaction, 4.0×10$^6$ RAW 264.7 cells were transfected with 5.0 mg plasmid DNA. Total RNA was isolated from the each well 48 h after transfection using RNeasy kit (Qiagen). DNase digestion with RNase-free DNaseI (Qiagen) was performed during RNA purification.

Primary data were processed using GeneCluster 2.0 software (Whitehead/MIT Center for Genome Research) to determine the average difference value and assess signal intensity for each probe set. We further performed clustering analysis using GeneSifter.

Immunoblotting and ELISA for Interleukin-1Beta

Cells were lysed in extraction buffer (20 mM Tris, 100 mM NaCl, 1% Triton X-100, 50 mg of NaF/ml, 1 mM Na3VO4, 0.2 mM phenylmethylsulfonyl fluoride, 10 mg of aprotinin/ml, and 10 mg of leupeptin/ml) 48 h after transfection. Protein concentration was determined for each sample using the BCA protein assay system (Pierce). Lysate samples containing same amount (100-200 mg) of protein were electrophoresed on 10% SDS-polyacrylamide gel, transferred to PVDF membranes, and reacted with anti-IL-1beta antibody (Santa Cruz Biotechnology). Blots were then reacted with a goat anti-rabbit IgG peroxidase-linked conjugate secondary antibody (Amersham, Arlington Heights, Ill.), and proteins were detected by chemiluminescence system (Western Lightning, PerkinElmer). We quantified IL-1beta protein production using ELISA system (eBioscience).

Real Time Quantitative PCR

After reverse transcription (RT) with total RNA from each reaction, real-time PCR was carried out using iQ™ SYBR Green Supermix (Bio-Rad, Hercules, Calif.) on MyiQ™ Single-Color Real-Time PCR Detection System (Bio-Rad). Final primer concentration was 300 nM each, and DNA content in each reaction was ideally 20 ng. To determine the relative expression levels of each transcript, we employed the comparative $C_T$ (fractional cycle number for which the amount of amplified target reaches a fixed threshold) method using GAPDH as a reference gene for normalization of each value owing to its stability in the experiment.

IL-1Beta Promoter Assay

Reporter plasmids contained various lengths of the mouse IL-1beta promoter region: IL-1beta 5'-flanking sequence (4093 bp and 50 bp from the transcription start site; −4093+1 CAT and −50+I CAT) and extended to the 5' portion of the second exon, terminating immediately upstream of the translation initiation codon, followed by the chloramphenicol acetyltransferase (CAT) gene and simian virus 40 splice and polyadenylation sites. The first intron is necessary for optimal CAT expression as previously described (Godambe, et al., *Mol. Cell Biol.* 15(1):112-119 (1995)). The same copy amount of each CAT plasmid (equal to 2.5 mg of −4093+1 CAT) was cotransfected with 2.5 mg of N3ICD in $4.0 \times 10^6$ RAW 264.7 cells. The IL-1beta promoter activity was determined 48 h after transfection using CAT ELISA (Roche) as instructed.

Transfection of siRNA Oligos for RBP-Jκ in Human Primary Macrophages

Human monocytes were isolated from human peripheral blood by density gradient centrifugation and adherence, then plated at $5 \times 10^6$ cells/well on plastic plates in RPMI 1640 medium containing 5% human serum and cultured for 14 days until they are fully differentiated to macrophages. We transfected siRNA oligos of human RBP-Jkappa (siGENOME™ SMARTpool siRNA, Dharmacon) in human macrophages to abolish RBP-Jkappa expression using the transfection reagent Lipofectamine™ 2000 (Invitrogen) as instructed. The final siRNA transfection medium contained 3 nM of siRNA oligos and 4 ul of Lipofectamine™ 2000 reagent in Opti-MEM (Gibco). Twenty-four hours after starting transfection, the transfection medium was completely replaced by the culture medium containing human serum again. We confirmed the inhibition of RBP-Jkappa expression in macrophage by real time PCR and Western blot 72 h after the medium exchange.

B. Results

RBP-Jkappa-Mediated Transcriptional Activation by N3ICD in Macrophages

We verified the expression of N3ICD using anti-FLAG antibody. Western blots showed the accumulation of N3ICD in the nucleus. We also confirmed the expression of Notch component genes including RBP-Jkappa and MAML1 in RAW 264.7 cells by RT-PCR. To examine whether N3ICD drives RBP-Jkappa-mediated transcriptional activation, we cotransfected N3ICD or vehicle plasmid (3.0 mg), CBF1-luc (1.0 mg), and pRL-SV40 (0.5 mg, an internal control) in $4.0 \times 10^6$ RAW cells as described. 48 h after the transfection, N3ICD significantly induced RBP-Jkappa-mediated transcription detected by the increase in luciferase activity indicating that NICD activates Notch signaling in macrophages.

Exploring Target Genes of Notch Signaling; Microarray Analysis and Real-Time PCR DNA microarray analysis revealed that Notch signaling increased or decreased a wide variety of genes in macrophages. We used N3ICD because our recent data indicated that Notch3 mRNA expression increased in human primary macrophages during differentiation, suggesting a potential role of Notch3 in macrophage biology. We calculated the fold difference in each probe set between the N3ICD-transfected and vehicle-transfected samples (n=3 each). Scatter plots showed the overall distribution of the genes arrayed on the chip. The core pathway of Notch signaling is mediated by RBP-Jkappa in association with other co-activators including MAML1 that functions as a transcriptional activator. This study primarily focused on the increased genes to explore the target genes under the regulation of Notch signaling. We categorized the increased genes according to the biological process in reference to Human Protein Reference Database (Peri, et al., *Genome Res.* 1300:2363-2371 (2003)). Notably, the genes involved in the immune response most remarkably increased. Some pro-inflammatory genes including IL-1kappa ranked among the most increased genes. Real-time PCR validated fold increases of mRNA expression of pro-inflammatory genes showing more than a four-fold increase on the DNA array [complement component 1 q subcomponent a, b and g (C1qa, C1qb, C1qg), IL-1beta, IL-1alpha, SAA3, CXCR4, MMP-9, and integrin-aL]. Fold increases obtained from the DNA microarray data correlated well to those of real-time PCR. On the other hand, according to the results of DNA microarray analysis and real-time PCR, N3ICD expression did not affect the mRNA expression of other pro-inflammatory genes such as TNF-alpha, IFN-gamma, and tissue factor, indicating the selective transcriptional regulation by Notch signaling. Examples of other increased genes, which may contribute to the macrophage-mediated inflammation, include MMP-8 (3.9 fold), CD97 (3.6 fold), platelet derived growth factor receptor beta (3.4 fold), IL-4 receptor (3.4 fold), histocompatibility 2, class II antigen A beta1 (3.3 fold), monocyte chemoattractant protein (MCP)-5 (3.1 fold), VLDL receptor (3.0 fold), MMP-3 (2.8 fold), CD27 (2.7 fold), syndecan-1 (2.6 fold), MMP-14 (2.4 fold), IL-7 receptor (2.4 fold), toll-like receptor 1 (2.3 fold), MCP-1 (2.3 fold), macrophage scavenger receptor type 1 (2.3 fold), insulin-like growth factor 1 receptor (2.2 fold), insulin-like growth factor 1 (2.1 fold), angiotensin II receptor, type I (2.1 fold), cathepsin H (2.1 fold), CD86 (2.1 fold). Jagged 1 (2.7 fold) and Delta-like 3 (2.6 fold), the Notch ligands, also increased.

NICD Induced IL-1β Expression in Murine Macrophages

We transfected various amounts of the N3ICD plasmid in RAW 264.7 cells (1.0, 3.0, and 5.0 mg plasmid DNA in $4.0 \times 10^6$ cells, respectively). N3ICD increased IL-1beta mRNA expression strikingly in a concentration-dependent manner, supporting the DNA microarray data. N1ICD and N2ICD also increased IL-1beta mRNA expression. Western blotting revealed a remarkable increase of the IL-1beta protein (pro-form; 31 kDa) 48 h after transfection. ELISA further quantified the IL-1beta protein production (in the whole cell lysate) and secretion (in the culture medium) induced by N3ICD. The magnitude of IL-1beta protein induction correlated well with that of mRNA levels. We further evaluated the promoter activity of mouse IL-1beta in RAW 264.7 cells using a CAT ELISA. N3ICD substantially increased the promoter activity and deletion of the 5' upstream (−50+I CAT) abolished the N3ICD-induced activity.

DNMAML-1 Inhibited NICD-Induced IL-1 Beta Expression

To determine whether the IL-10 induction involves the Notch-RBP-Jkappa mediated core pathway, we cotransfected DNMAML-1 (2.5 mg) and N3ICD (2.5 mg) in addition to RBP-Jkappa-luc (1.0 mg) and pRL-SV40 (0.5 mg) vectors in RAW 264.7 cells. Transfection of DNMAML-1 (2.5 mg) and N3ICD (2.5 mg) plasmids in $4.0 \times 10^6$ cells almost completely abolished the increase in IL-1beta mRNA expression 48 h after transfection. DNMAML1 recruits NICD and binds to RBP-Jkappa, then antagonizes the binding of other essential cofactors such as CBP/p300. Hence, it is assumed that the ternary complex composed of NICD, DNMAML-1, and RBP-Jkappa does not function as a transcriptional activator. DNMAML-1 also abolished IL-1beta induction by N1ICD and N2ICD in the same manner. These results indicate the IL-1beta induction by NICD depends on the RBP-Jkappa and MAML1-mediated pathway.

Notch-Mediated Increases of Various Proinflammatory Genes

We also validated dose-dependent increases of various increased genes [C1qa, C1qb, C1qg, IL-1alpha, IL-10, H2-IEa, CXCR4, CD97, Integrin-alpha L, Aif-1, and Nuclear receptor subfamily 1, group H, member 3 (Nr1 h3)] by N3ICD in RAW 264.7 cells by transfection various amounts of the N3ICD plasmid in RAW 264.7 cells (1.0, 3.0, and 5.0 mg plasmid DNA in $4.0 \times 10^6$ cells, respectively). N1ICD and N2ICD (5.0 mg plasmid DNA in $4.0 \times 10^6$ cells) also increased these genes in the same manner. DNMAML1 abolished the increases of these genes in the same manner as of IL-1beta indicating the specific regulation of these increased genes by Notch signaling.

Induction of IL-1Beta mRNA in Human Primary Macrophages

To determine whether Notch signaling induces IL-1beta expression in human macrophages, we performed co-culture experiments using MS5-Dll4 cells and human primary macrophages derived from peripheral blood monocytes. Dll4 binding increased IL-1beta mRNA expression in human macrophages determined by real-time RT-PCR (6 h, 98.2 fold, n=10, p<0.01).

C. Discussion

This study explored the mechanism of macrophage activation through Notch signaling, and demonstrates that Notch signaling may regulate various pro-inflammatory genes, including IL-1beta, a novel target gene of this signaling pathway in any cell type. The results suggest a role of Notch signaling in inflammation and atherosclerosis through macrophage activation. In addition, the results of DNA microarray analysis, suggest that Notch signaling may regulate, directly and indirectly, various genes associated with inflammation over various functional categories, including the immune response (e.g., C1q, IL-1beta, IL-1alpha), signal transduction (e.g., Nr1 h3, CXCR4, allograft inflammatory factor1), transport (e.g., serum amyloid A3), protein metabolism (e.g., MMP-9), cell growth and/or maintenance (e.g., myristoylated alanine rich protein kinase C).

Example 3

Studies Related to Vein Graft Failure

The present example examines the hypothesis that Notch signaling promotes vein graft disease. It was found that Dll4 antibody administration for 28 days inhibited lesion development of vein grafts in LDL-receptor deficient (Ldlr−/−) mice, and suppressed macrophage accumulation and macrophage expression of pro-inflammatory M1 genes. Dll4 antibody treatment for 7 days after grafting also reduced macrophage burden at Day 28. Dll4 silencing via macrophage-targeted lipid nanoparticles reduced lesion development and macrophage accumulation. Gain-of-function and loss-of-function studies suggested in vitro that Dll4 induces pro-inflammatory molecules in macrophages. Macrophage Dll4 also stimulated smooth muscle cell (SMC) proliferation and migration and suppressed their differentiation. It may be concluded that macrophage Dll4 promotes the lesion development of vein graft, supporting the Dll4-Notch axis as a novel therapeutic target.

A. Methods

Vein Graft Implantation

The Harvard Medical Area Standing Committee on Animals reviewed and approved all animal experimental protocols. Male LDL receptor-deficient (Ldlr−/−) mice with C57Bl/6 background were purchased from Jackson Laboratory (Bar Harbor, Me.) and maintained with water ad libitum. High-fat diet containing 1.25% cholesterol (D12108; Research Diets, NJ) was started at 12 weeks of age, both in donor and recipient Ldlr−/− mice. After 2 weeks of high-fat diet feeding, vein graft implantation was performed as previously reported (Yu, et al., *J. Vasc. Surg.* 52:444-452 (2010); Yu, et al., *Surgery* 153:63-69 (2013)). Inferior vena cava (IVC) was harvested from age-matched donor Ldlr−/− mice and implanted into the recipient right carotid artery with small cuffs made from polyetheretherketone (Zeus, Orangeburg, S.C.). After vein graft implantation, blood flow and pulsation of the graft was visually assessed to confirm successful grafting. For the selective blockade of Dll4, we intraperitoneally administered hamster anti-mouse Dll4 antibody (250 µg per injection) (HMD4-2, Bio X Cell, West Lebanon, N.H.) (Fukuda, et al., *Proc. Nat'l Acad. Sci. USA* 109:E1868-1877 (2012); Fukushima, et al., *Immunol. Lett.* 121:140-147 (2008); Oishi, et al., *Pancreas.* 39:897-903 (2010)) twice a week. Non-immune hamster IgG antibody (Bio X Cell) was administered to control mice with the same regimen.

Histopathology and Immunohistochemistry

Vein grafts were harvested 28 days after vein graft implantation. After perfused fixation with 10% neutral buffered formalin, grafts were incubated with 15% and 30% sucrose for 24 hours each. Then, grafts were embedded and frozen in OCT compound. Sections for morphometric analysis were cut with 7 µm thickness. Lesion size was analyzed with 30 µm intervals after 300 µm trimming from the distal edge of proximal cuff. After Masson-Trichrome staining, 8 sections per each graft were analyzed and average values were used for statistical analysis. The border between intima and media/adventitia was determined by the internal elastic lamina as previously reported (Yu, et al., *J. Vasc. Surg.* 52:444-452 (2010)). The area of lumen, intima and media/adventitia were determined by Image J software. Several variables including intimal thickness, luminal diameter and vessel diameter were calculated based on these measured values as previously reported (Yu, et al., *J. Vasc. Surg.* 52:444-452 (2010)). Immunostaining was also performed with frozen sections cut with 7 μm thickness in mice. Macrophages were stained with rat anti-Mac-3 monoclonal antibody (BD Pharmingen, San Diego, Calif.). Vascular SMCs were stained with rabbit polyclonal anti-α-SMA actin antibody (Thermo Fisher Scientific Inc., Waltham, Mass.) or mouse monoclonal anti-human SMA (1A4) antibody (DAKO, Denmark). Dll4 was stained with rabbit polyclonal anti-Dll4 antibody (Abcam, Cambridge, Mass.) and cleaved Notch1 was stained with rabbit polyclonal anti-Notch1 (cleaved N-terminus) antibody (EMD Millipore, Billerica, Mass.). Proliferating cells were evaluated with mouse polyclonal anti-proliferation cell nuclear antigen (PCNA) antibody (DAKO) with "Mouse on Mouse" staining kit (Vector Laboratories) or rabbit anti-PCNA antibody (Abcam). In fluorescent immuno-staining, antibodies conjugated with Alexa Fluor 488 or 568 (Life technologies, Carlsbad, Calif.) were used as secondary antibodies. Isolated human saphenous vein grafts were used for histochemical analysis under the approval of institutional review board of Brigham and Women's Hospital. Vein grafts were fixed with 10% neutral buffered formalin, embedded in paraffin and cut with 5 μm thickness. Dll4 was stained with rabbit polyclonal anti-Dll4 antibody (Abcam). Macrophage and SMC were stained with mouse monoclonal anti-human CD68 antibody and mouse monoclonal anti-human SMA (1A4) antibody (DAKO).

Cell Isolation from Vein Graft

Vein grafts were cut into small pieces and incubated with enzyme solution including 400 unit/ml collagenase type II and 0.75 unit/ml elastase (Worthington Biochemical, Lakewood, N.J.) for 1 hour at 37° C. After filtration through a 40-μm cell strainer (BD Pharmingen), cells were used for further experiments. In real-time PCR of isolated macrophages, F4/80 positive macrophages were isolated by magnetic sorting. PE-conjugated anti-F4/80 antibody (Biolegend, San Diego, Calif.) were used as the primary antibody to specifically select macrophages.

Semi-Quantitative Real-Time PCR

RNA was extracted from tissues or cells by illustra RNAspin Mini Kit (GE Healthcare, Little Chalfont, UK), and cDNA was synthesized by High Capacity cDNA Reverse Transcription Kit (Life Technologies). Semi-quantitative real-time PCR was performed with a MyiQ single-color real-time PCR detection system (BioRad, Hercules, Calif.) and PerfeCTa SYBR Green SuperMix for iQ (Quanta Biosciences, Gaithersburg, Md.). Primer designs are listed on supplemental table 1. Data were calculated by ΔΔCT method and expressed in arbitrary units that were normalized by β-actin or GAPDH.

TABLE 1

Primers for semi-quantitative real time PCR

| Gene Abbr | Gene Name | Forward primer | Reverse primer |
|---|---|---|---|
| Actb | β-actin | 5'-CCTGAGCGCAAGTACTCTGTGT-3' (SEQ ID NO: 1) | 5'-GCTGATCCACATCTGCTGGAA-3' (SEQ ID NO: 2) |
| Dll4 | delta-like 4 | 5'-ACCTTTGGCAATGTCTCCAC-3' (SEQ ID NO: 3) | 5'-GTTTCCTGGCGAAGTCTCTG-3' (SEQ ID NO: 4) |
| Hes1 | Hes1 | 5'-ACACCGGACAAACCAAAGAC-3' (SEQ ID NO: 5) | 5'-ATGCCGGGAGCTATCTTTCT-3' (SEQ ID NO: 6) |
| Hey1 | Hey1 | 5'-GGTACCCAGTGCCTTTGAGA-3' (SEQ ID NO: 7) | 5'-ATGCTCAGATAACGGGCAAC-3' (SEQ ID NO: 8) |
| Hey2 | Hey2 | 5'-GTTCCGCTAGGCGACAGTAG-3' (SEQ ID NO: 9) | 5'-TGCCCAGGGTAATTGTTCTC-3' (SEQ ID NO: 10) |
| Il1b | Interleukin-1β | 5'-GCCCATCCTCTGTGACTCAT-3' (SEQ ID NO: 11) | 5'-AGGCCACAGGTATTTTGTCG-3 (SEQ ID NO: 12)' |
| Il6 | Interleukin-6 | 5'-AGTTGCCTTCTTGGGACTGA-3' (SEQ ID NO: 13) | 5'-TCCACGATTTCCCAGAGAAC-3' (SEQ ID NO: 14) |
| Tnf | Tumor necrosis factor-α | 5'-AGCCCCCAGTCTGTATCCTT-3' (SEQ ID NO: 15) | 5'-CTCCCTTTGCAGAACTCAGG-3' (SEQ ID NO: 16) |
| Ccl2 | Monocyte chemoattractant protein-1 | 5'-AGGTCCCTGTCATGCTTCTG-3' (SEQ ID NO: 17) | 5'-TCTGGACCCATTCCTTCTTG-3' (SEQ ID NO: 18) |
| Mmp2 | Matrix metalloproteinase-2 | 5,-CCCCATGAAGCCTTGTTTACC-3' (SEQ ID NO: 19) | 5'-TTGTAGGAGGTGCCCTGGAA-3' (SEQ ID NO: 20) |
| Mmp9 | Matrix metalloproteinase-9 | 5'-GAAGGCAAACCCTGTGTGTT-3' (SEQ ID NO: 21) | 5'-AGAGTACTGCTTGCCCAGGA-3' (SEQ ID NO: 22) |
| Mmp13 | Matrix metalloproteinase-13 | 5'-GAGCCACAGATGAGCACAGA-3' (SEQ ID NO: 23) | 5'-ATGTAAGGCCACCTCCACTG-3' (SEQ ID NO: 24) |
| Serpine1 | Plasminogen activator inhibitor-1 | 5'-ACGTTGTGGAACTGCCCTAC-3' (SEQ ID NO: 25) | 5'-GCCAGGGTTGCACTAAACAT-3' (SEQ ID NO: 26) |

TABLE 1-continued

Primers for semi-quantitative real time PCR

| Gene Abbr | Gene Name | Forward primer | Reverse primer |
|---|---|---|---|
| F3 | Tissue factor | 5'-TCCTGGCCACCATCTTTATC-3' (SEQ ID NO: 27) | 5'-ATGTTGCACAGTTCCCATCA-3' (SEQ ID NO: 28) |
| Pdgfb | Platelet-derived growth factor-β | 5'-ACGTTGTGGAACTGCCCTAC-3' (SEQ ID NO: 29) | 5'-GCCAGGGTTGCACTAAACAT-3' (SEQ ID NO: 30) |
| Arg1 | Arginase-1 | 5'-TCACCTGAGCTTTGATGTCG-3' (SEQ ID NO: 31) | 5'-CACCTCCTCTGCTGTCTTCC-3' (SEQ ID NO: 32) |
| Chi3l3 | Ym-1 | 5'-GAAGGAGCCACTGAGGTCTG-3' (SEQ ID NO: 33) | 5'-CACGGCACCTCCTAAATTGT-3' (SEQ ID NO: 34) |
| Ccr2 | chemokine (C-C motif) receptor 2 | 5'-CCTGCAAAGACCAGAAGAGG-3' (SEQ ID NO: 35) | 5'-TATGCCGTGGATGAACTGAG-3' (SEQ ID NO: 36) |
| Acta2 | α-smooth muscle actin | 5'-CTTCGCTGGTGATGATGCTC-3' (SEQ ID NO: 37) | 5'-TTGGTGATGATGCCGTGTTC-3' (SEQ ID NO: 38) |
| Tagln | SM22α | 5'-CAAGCCTTCTCTGCCTCAAC-3' (SEQ ID NO: 39) | 5'-TCGATCCCTCAGGATACAGG-3' (SEQ ID NO: 40) |
| Cnn1 | Calponin-1 | 5'-GGGGACACTTAGACCCTTGA-3' (SEQ ID NO: 41) | 5'-GCCATACCTGCAGTCCAATG-3' (SEQ ID NO: 42) |
| Myh11 | Smooth muscle myosin heavy chain | 5'-GTCTCCAGCACAAATGCTCA-3' (SEQ ID NO: 43) | 5'-AGTACACGTCAGGGGCAATC-3' (SEQ ID NO: 44) |

Molecular Imaging on Macrophage Activation

Intravital microscopy (IVM) was performed to evaluate macrophage accumulation and matrix metalloproteinase (MMP) activity in vivo, as previously reported (Quillard, et al., *Arterioscler. Thromb. Vasc. Biol.* 31:2464-2472 (2011)). We used near-infrared fluorescent nanoparticles—Aminospark 750 (Ex/Em=753/773 nm) and MMP sense 680 (Ex/Em=680/700 nm) (PerkinElmer, Inc., Waltham, Mass.). These nanoparticles were administered via tail vein 24 hours before imaging. After surgical exposure of the vein graft, fluorescent signals from these nanoparticles were captured by confocal laser microscopy (Olympus FV1000).

Collagen Hue Analysis

In sections stained with picrosirius red (Polyscience, Inc., Warrington, Pa.), fibrillar collagen was observed under a circularly polarized microscope with green and red optic filters (HQ535/50m, D605/55m, Chroma), as previously described (Quillard, et al., *Arterioscler Thromb. Vasc. Biol.* 31:2464-2472 (2011); Aikawa, et al., *Circulation* 97:2433-2444 (1998)). As the thickness of collagen fiber increases, the color shifts from green to red. Collagen volume was quantified by image analysis software (NIS-Elements, Nikon).

Preparation of Human Primary Macrophages

Human primary macrophages were prepared as previously described (Fung, et al., *Circulation* 115:2948-2956 (2007)). Briefly, blood mononuclear cells were isolated by density gradient centrifugation. Then, isolated cells were plated on culture dishes and adherent cells were cultured with RPMI1640 (Life Technologies) containing 5% human serum and 1% penicillin/streptomycin for 10 to 14 days before experiments.

Gain-of-Function and Loss-of-Function Experiments in Mouse Primary Macrophages

Peritoneal macrophages were prepared for in vitro gain-of-function and loss-of-function studies as previously described (Koga, et al., *Hypertens. Res.* 31:1791-1800 (2008); Koga, et al., *Arterioscler. Thromb. Vasc. Biol.* 29:458-464 (2009)). Brewer thioglycollate medium (BD Diagnostic Systems, Sparks, Md.) was injected into the peritoneal cavity of C57Bl/6 mice 4 days before macrophage collection. Ice-cold phosphate-buffered saline (PBS) was injected into the peritoneal cavity and cells were thus harvested. Then, the cells were washed with PBS and plated on 48-well culture dishes for further experiments. Cells were cultured with RPMI1640 containing 10% fetal bovine serum (FBS) and overnight starvation was performed with 0.5% FBS before each experiment. In gain-of-function experiments, Dll4 plasmid (0.4 μg/well) or control plasmid was transfected with lipofectamine 2000 (Life Technologies) according to the manufacture's instruction and mRNA was quantified 24 hours later. Dll4 expression was verified by immunofluorescent imaging with rabbit anti-Dll4 antibody (Abcam) and Alexa Fluor 568 goat anti-rabbit IgG (Life Technologies). In loss-of-function experiments, peritoneal macrophages were incubated with Dll4 blocking antibody (50 μg/mL) or isotype IgG for 4 hours, and then mRNA was extracted for quantitative analysis.

In PDGF-B experiments, transient overexpression of Dll4 or Dll4 stimulation by immobilized Dll4 was performed to RAW264.7 cells. Dll4 immobilization was performed by overnight pre-incubation of cell culture plates with 2 μg/mL recombinant mouse Dll4 (R&D systems, Minneapolis, Minn.).

In culture experiments of human cells, saphenous vein SMCs (HSVSMCs) and saphenous vein endothelial cells (HSVECs) were isolated as previously described (Sukhova et al., *J. Clin. Invest.* 102:576-583 (1998); Shi, et al., *Circ. Res.* 92:493-500 (2003)). HSVSMCs were cultured in Dulbecco's modified Eagle's medium (DMEM) (Life Technologies) containing 10% FBS, 1% non-essential amino acid solution, 1% pyruvate and 1% penicillin/streptomycin. HSVECs were cultured in M199 medium (Life Technologies) containing 20% FBS, 1% L-glutamine, 1% penicillin/streptomycin, 50 μg/ml endothelial cell growth supplement (Biomedical Technologies, Stoughton, Mass.), and 100

μg/ml heparin. In gain-of-function studies, these cells were plated on top of immobilized human Dll4 protein (2 μg/mL) (R&D systems). In loss-of-function studies, cells were incubated with 10 μg/mL mouse anti-human Dll4 antibody (MHD4-46) (Oishi, et al., *Pancreas.* 39:897-903 (2010)). RNA was extracted at indicated time points.

Indirect Co-Culture Experiments

Mouse aortic SMCs were prepared, as described previously (Shimizu, et al., *Circulation* 120:1800-1813 (2009)), and cultured with DMEM containing 10% FBS, 1% non-essential amino acid solution, 1% pyruvate, and 1% penicillin/streptomycin. All experiments were performed with SMCs between 3 to 10 passages, and 3 hours starvation was performed before experiments with DMEM containing 0.1% FBS. To collect conditioned media, RAW264.7 cells were cultured with DMEM containing 0.1% FBS after transfection of Dll4 or control plasmid. Plasmid transfection was performed with lipofectamine 2000 according to the manufacturer's instruction. Condition media were centrifuged at 1,500 g for 5 minutes and transferred to the culture dishes of SMCs 48 hours after transfection. To examine the SMC proliferation, $5 \times 10^3$ cells were plated on 96-well culture dishes. After 12 hours starvation, conditioned media were added into the culture dishes. 10% FBS was added as a positive control. Cell proliferative ability was evaluated 24 hours later by Non-Radioactive Cell Proliferation Assay kit (Promega, Madison, Wis.) (Takeda, et al., *Nature* 479:122-126 (2011)). SMC migration was examined by the modified Boyden's chamber method with 8 μm pore chemotaxis chambers (Neuro Probe, Gaithersburg, Md.). Conditioned media were placed in the lower chamber and $5 \times 10^4$ SMCs were placed on type I collagen pre-coated membrane. Cell migration was quantified as the number of SMCs migrated to the lower surface of the membrane after 4 hours incubation. Migrated cells were fixed with methanol and stained with 0.25% crystal violet/50% methanol. Then, number of cells was counted under microscope and for each sample, the average of 3 high power fields was used for analysis (Takeda, et al., *Nature* 479:122-126 (2011); Goncharova, et al., *Nat. Protoc.* 1:2933-2939 (2006)). The differential state of SMC was examined by quantification of SMC markers including α-SMA, smooth muscle 22-α (SM22α, Calponin-1 and smooth muscle myosin heavy chain (SM-MHC). SMCs ($8 \times 10^4$ cells/well) were plated on a 24-well plate and incubated for 24 hours at 37° C. After 3 hours starvation, SMCs were stimulated with conditioned media for 24 hours. Then, RNA was extracted for quantitative real-time PCR analysis (Takeda, et al., *Nature* 479:122-126 (2011)).

Western Blotting

Total cellular protein was collected from RAW264.7 cells at 4° C. in M-PER Mammalian Protein Extraction Reagent (Thermo Fisher Scientific) containing 1% Halt Protease Inhibitor Cocktail (Thermo Fisher Scientific). Protein concentration was determined by BCA protein assay and 20 μg of sample protein was then loaded onto each lane. Blots were stained with antibody specific for PDGF-B (LifeSpan BioSciences, Seattle, Wash.) and β-actin was used as an intrinsic control. Following incubation with HRP-tagged secondary antibody (Thermo Fisher Scientific), an ECL detection kit (Perkin Elmer) was used to reveal antibody binding.

Figure 12:
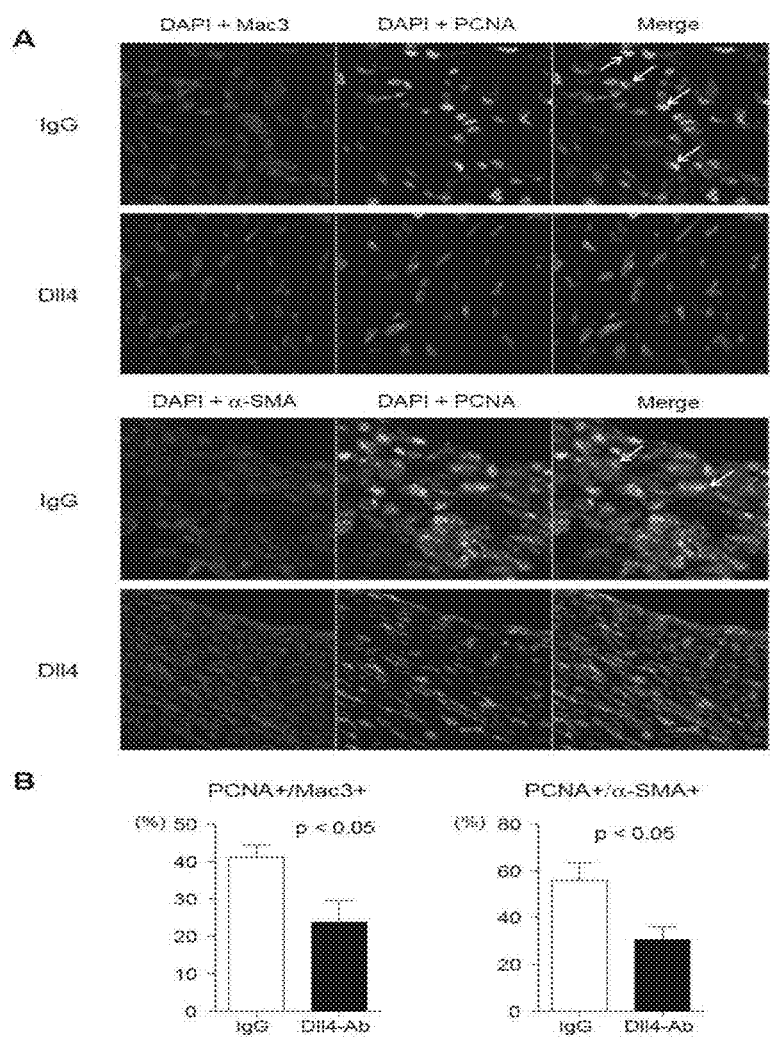
FIG. 12: Macrophage and SMC proliferation in vein grafts of mice treated with control IgG or Dll4 blocking antibody for 28 days. (A) Upper panels show double staining of Mac-3 and PCNA. Arrows indicates double-positive cells. Lower panels show double staining of α-SMA and PCNA. (B) The percentage of PCNA-positive cells in Mac-3 or α-SMA-positive cells. N=5 or 6.

Formulation of Lipid Nanoparticles siRNA targeting mouse Dll4 sequence NM 019454, and non-targeting control siRNA (modified to avoid immune stimulation and off-target effects) were synthesized as previously described (Leuschner, et al., *Nat. Biotechnol.* 29:1005-1010 (2011); Frank-Kamenetsky, et al., *Proc. Natl Acad. Sci. USA* 105:11915-11920 (2008); Whitehead, et al., *Annu. Rev. Chem. Biomol. Eng.* 2:77-96 (2011)). Macrophage-targeted lipid nanoparticles were prepared and mixed with siRNA, as previously described (Leuschner, et al., *Nat. Biotechnol.* 29:1005-1010 (2011); Love, et al., *Proc. Natl Acad. Sci. USA* 107:1864-1869 (2010)) to prepare siRNA encapsulated lipid nanoparticles. More specifically, the lipid-like material AF12 was mixed with cholesterol, polyethylene glycol (PEG), and disteroylphosphatidyl choline (DSPC) at a molar ratio of 50:38.5:1.5:10. This mixture was combined with siRNA in a microfluidic device to produce nanoparticles (Chen, et al, *J. Am. Chem. Soc.* 134:6948-6951 (2012)). After nanoparticle formulation, particle size was characterized with dynamic light scattering. Both control siRNA- and Dll4 siRNA-nanoparticles had an average diameter of 45 nm (FIG. 12).

Kinetic Study of Lipid Nanoparticle

Kinetics and cell specificity were analyzed with AF12 nanoparticles incorporating Dll4 siRNA. In the kinetics study, 0.5 mg/kg particles were injected via tail vein and splenic macrophages were collected by magnet beads sorting (EasySep system, StemCell Technologies, Vancouver, Canada). In the specificity study, Ldlr−/− mice were fed high-fat diet and vein graft implantation was performed as described above. AF12 nanoparticles incorporating control siRNA or Dll4 siRNA was administered 21 and 24 days after vein grafting. Vein grafts were harvested 28 days after grafting and endothelial cells/macrophages were dissected by laser capture microdissection (LMD6500, Leica, Germany). Vein graft was collected and snap-frozen in OCT compound. Intimal tissues which contain macrophages or endothelial cells were collected by laser capture microdissection to examine in vivo specificity of siRNA nanoparticles. Dissecting sites were determined according to the Mac-3 immunostaining of the adjacent section to dissect macrophages selectively. The layer including luminal surface was considered as an endothelial layer. RNA was extracted from dissected tissues and cDNA was synthesized as described above. cDNA was pre-amplified with PerfeCTa PreAmp SuperMix (Quanta Biosciences) and then Dll4 mRNA was quantified by real-time PCR.

Statistical Analyses

All data are reported as the mean±SEM for continuous variables. We have evaluated all the data about their normality and in case they are expected not to follow Gaussian distribution, we have performed non-parametric test (Mann-Whitney test) for a comparison of two groups. In case the data follows Gaussian distribution, statistical analysis of differences between two groups was performed by Student's t test. Comparisons between three or more groups, one-way ANOVA with Bonferroni post-test were used for the analyses. Probability values less than 0.05 were considered to be statistically significant.

B. Results

Increased Expression of Dll4 in Macrophages in Human and Mouse Vein Grafts

Figure 8:
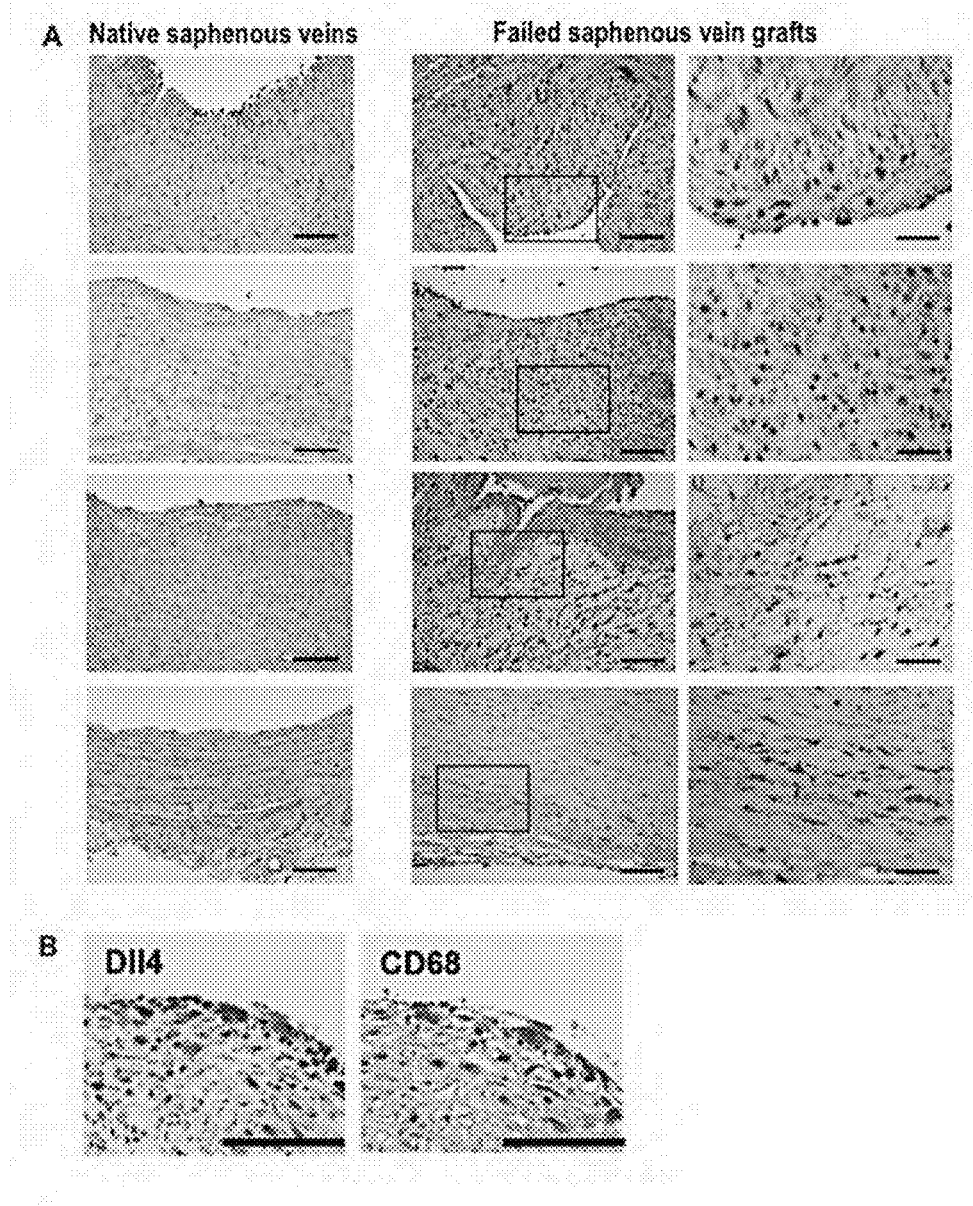
FIG. 8: Dll4 expression increases in human vein grafts. (A) Human SVG harvested for bypass surgery (control native vein, left) and failed SVG (middle and right). Sections were stained with anti-Dll4 antibody. Right images show high magnification images in rectangles. Scale bars indicate 100 μm (left and middle) and 50 μm (right). (B) Serial section of failed human SVG stained with anti-Dll4 and anti-CD68 antibodies. Scale bar indicates 100 μm.
Figure 9:
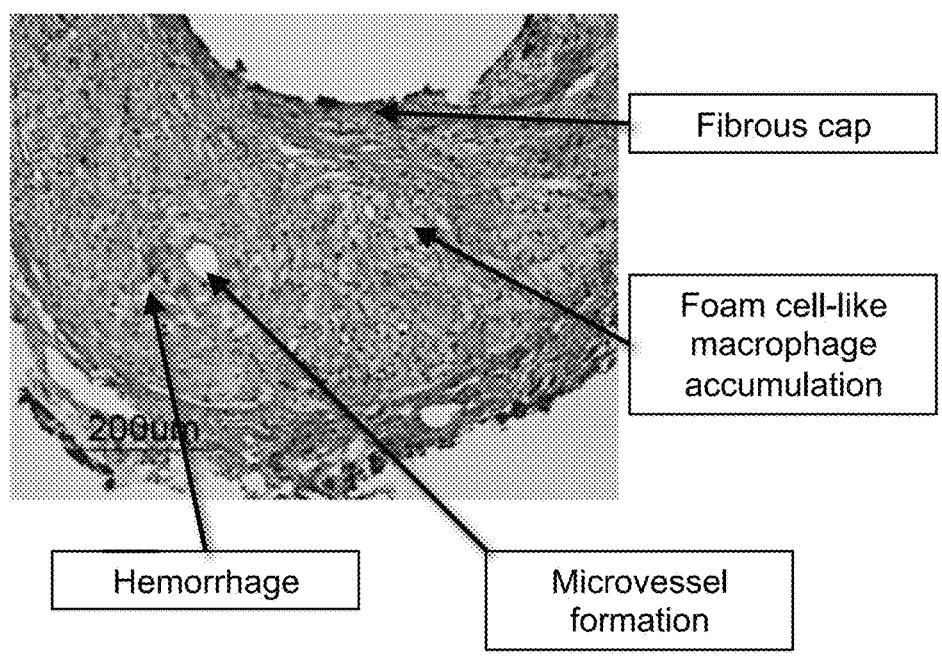
FIG. 9: The neointima of vein grafts in Ldlr−/− mice shows features associated with advanced atherosclerotic lesions. IVCs from donor Ldlr−/− mice were implanted into the carotid artery of recipient Ldlr−/− mice after 2 weeks of high fat diet feeding. Vein grafts were harvested 28 days after implantation and then stained by Masson-Trichrome staining. Scale bar indicates 200 μm.
Figure 10:
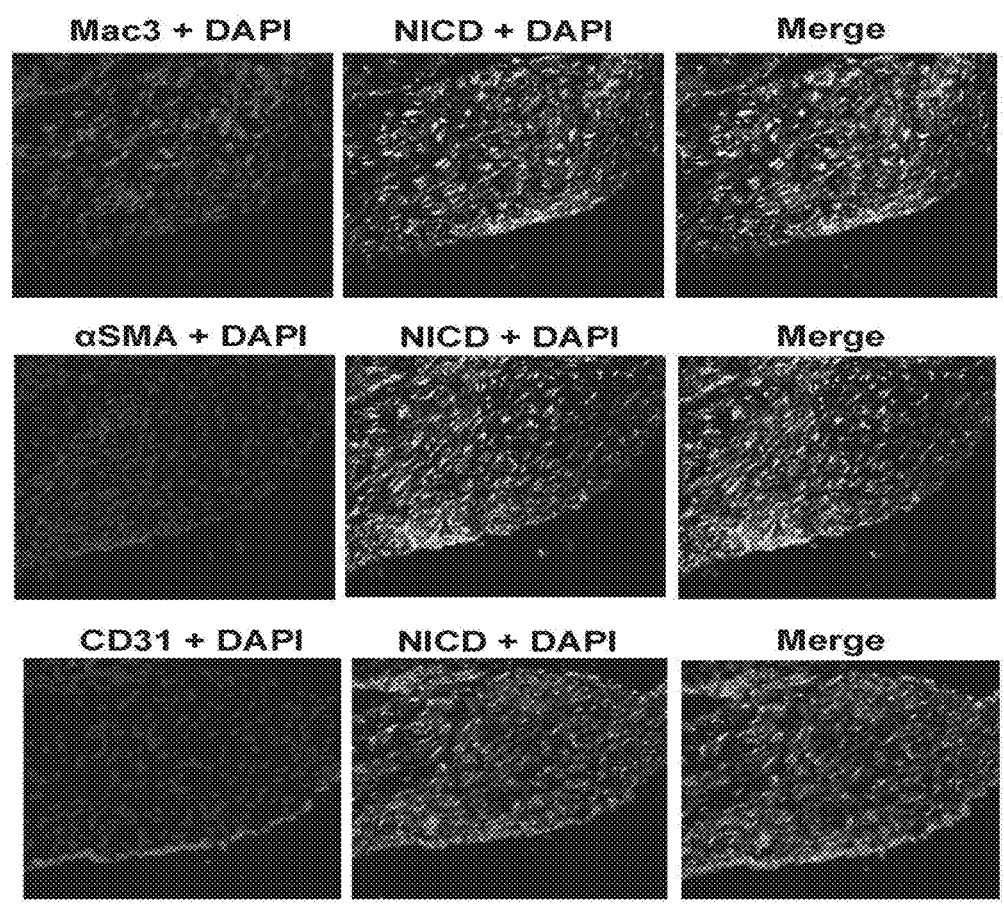
FIG. 10: Notch1 intracellular domain (NICD) in macrophages, smooth muscle cells and endothelial cells in vein grafts of mice treated with control IgG or Dll4 blocking antibody for 28 days. Upper panels show double staining of Mac-3 and Notch1 NICD. Middle panels show double staining of α-SMA and Notch1 NICD. Lower panels show double staining of CD31 and Notch1 NICD. Arrows indicate double-positive cells. Scale bars indicate 20 μm.
Figure 11:
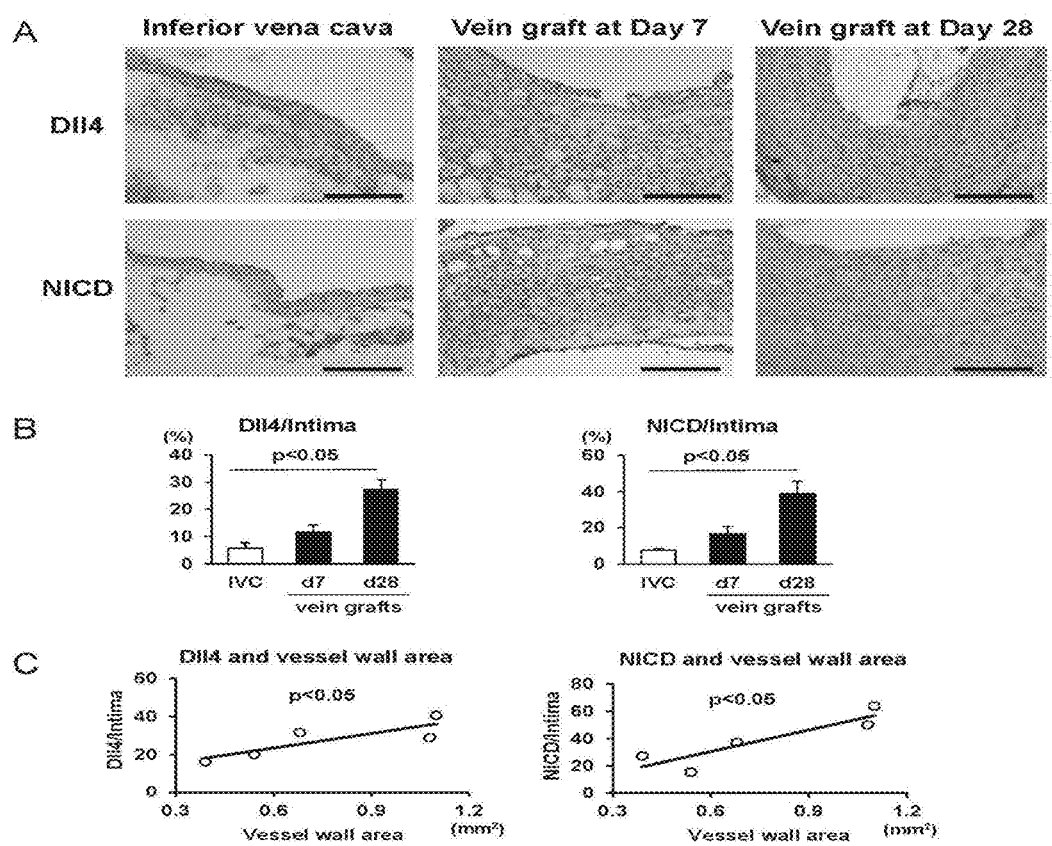
FIG. 11: The expression of Dll4 and Notch 1 intracellular domain (NICD) increase in mouse vein grafts. (A) Immunostaining of Dll4 and NICD in inferior vena cava (IVC), and vein grafts at day 7 and 28. Scale bars indicate 100 μm. (B) Bar graphs show quantification of Dll4 and Notch 1 NICD as a percentage of the positive area in intima in IVCs and vein grafts at days 7 and 28 (n=5 to 6). (C) Figures show the association of Dll4- or Notch 1 NICD-positive area and vessel wall area of the ultrasound data in vein grafts at day 28 (n=5).

In control human saphenous veins before grafting, little if any intimal cells were immunoreactive for Dll4, whereas the thickened intima of failed human SVGs contained many cells expressing Dll4 (FIG. 1, panel A; FIG. 8). In the failed grafts, some CD68-positive intimal macrophages were immunoreactive to Dll4 antibody (FIG. 8, panel B). In high-cholesterol/high-fat-fed Ldlr−/− mice, IVC implanted into the carotid artery developed more advanced lesions than in wild-type mice (Yu, et al., *J. Vasc. Surg.* 52:444-452 (2010)). The neointima of vein grafts in Ldlr−/− mice showed features associated with advanced arterial plaques prone to rupture, including foam cell accumulation, microvessels, and intraplaque hemorrhage (FIG. 9), supporting previous reports on a similar model in hypercholesterolemic ApoE3*Leiden mice by the Paul Quax group (Eefting, et al., *J. Vasc. Surg.* 50:152-160 (2009); de Vries, et al., *PLoS One.* 7:e47134 (2012)). Vein grafts of Ldlr−/− mice expressed higher levels of Dll4 mRNA compared to native IVC of Ldlr−/− or wild-type mice (qPCR, FIG. 1, panel B). In mouse vein grafts, Dll4 localized primarily to intimal macrophages while smooth muscle cell (SMC) expression of Dll4 was minimal (Day 28, FIG. 1, panel C). Ligand binding promotes the cleavage of Notch receptors and release of the intracellular domain (Thurston, et al., *Nat. Rev. Cancer* 7:327-331 (2007)). The amount of Notch1 intracellular domain (NICD), as identified by the antibody that recognizes the neoepitope, thus indicates the levels of Notch signaling activation. NICD accumulated primarily in intimal macrophages of vein grafts 28 days after implantation, while few if any smooth muscle cells (SMC) and endothelial cells (EC) were stained positively (FIG. 10). The amounts of Dll4 and NICD in the intima of mouse vein grafts increased in parallel over time FIG. 11, panels A and B), indicating acceleration of Notch activation during the lesion development. Furthermore, the amounts of Dll4 correlated positively with the wall area (FIG. 11, panel C). These results suggest that Dll4 expression increases during the development of vein graft lesions.

Blockade of Dll4 Reduces Lesion Formation and Inflammation in Vein Grafts

Blocking antibody for Dll4 (Fukuda, et al., *Proc. Nat'l Acad. Sci. USA* 109:E1868-1877 (2012); Fukushima, et al., *Immuno. Lett.* 121:140-147 (2008); Yamanda, et al., *Blood* 113:3631-3639 (2009)) was administered to Ldlr−/− mice twice a week for 28 days. Reduced amounts of NICD following antibody administration indicate that Dll4 mediates Notch activation in vein graft lesions (FIG. 1, panel D). Dll4 blockade produced no effects on serum levels of total cholesterol (801.0±51.5 vs. 867.0±15.7 mg/dL), triglycerides (216.2±19.3 vs. 249.3±36.1 mg/dL), and body weight (29.6±0.7 vs. 30.5±1.1 g). We previously verified that administration of the same antibody for 3 months did not affect blood pressure, food consumption, and physical activity in Ldlr−/− mice (Fukuda, et al., *Proc. Nat'l Acad. Sci. USA* 109:E1868-1877 (2012)).

Figure 2:
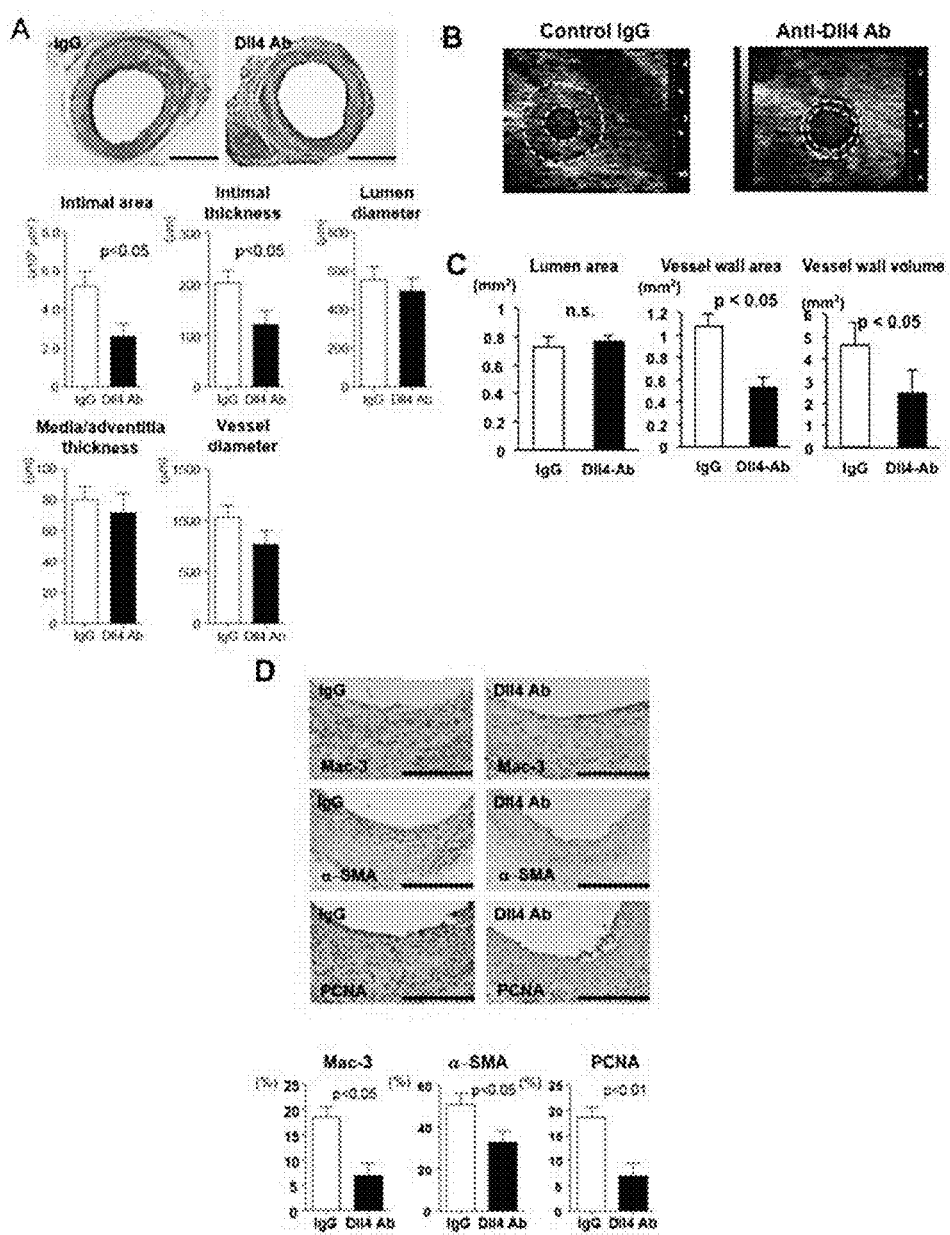
FIG. 2: Antibody blockade of Dll4 for 28 days inhibits lesion formation in vein grafts. (A) Vein graft harvested 28 days after implantation from control IgG or Dll4 antibody-treated animals and results of morphometric analyses. Scale bar indicates 400 µm. n=10 and 9. (B) Ultrasound images of vein grafts treated with control IgG (left) and anti-Dll4 antibody (right) after 28 days. The dotted lines indicate vessel wall area. (C) Lumen and vessel wall area (mm$^2$), and vessel wall volume (mm$^3$) were measured by ultrasound in control IgG or Dll4 antibody treated vein graft (n=5 and 3). (D) Immunostaining of Mac-3, α-SMA, and PCNA at day 28 and quantitative data shown as percentages of staining positive area (Mac-3, α-SMA) and PCNA positive nucleus in the intima. Scale bar indicates 200 µm. n=4 to 7.

28 days of Dll4 antibody treatment decreased the area and thickness of the intima of vein grafts of Ldlr−/− mice (FIG. 2, panel A). Noninvasive ultrasonography visualized decreased wall area and volume of the vein grafts in mice treated with Dll4 antibody and supported the histologic data (FIG. 2, panels B and C). Dll4 blockade also reduced macrophage accumulation, SMC accumulation, and cell proliferation (FIG. 2, panel D). Proliferation of macrophages and SMCs may contribute to the pathogenesis of vascular diseases (Rosenfeld, et al., *Arteriosclerosis* 10:680-687 (1990); Luscher, *Curr. Opin. Cardiol.* 6:868-876 (1991); Aikawa, et al., *Circulation* 103:276-283 (2001); Robbins, et al., *Nat. Med.* 19:1166-1172 (2013)). Blockade of Dll4 reduced proliferating Mac-3 positive and α-SMA positive cells, as demonstrated by double immunofluorescence with PCNA (FIG. 12).

Figure 13:
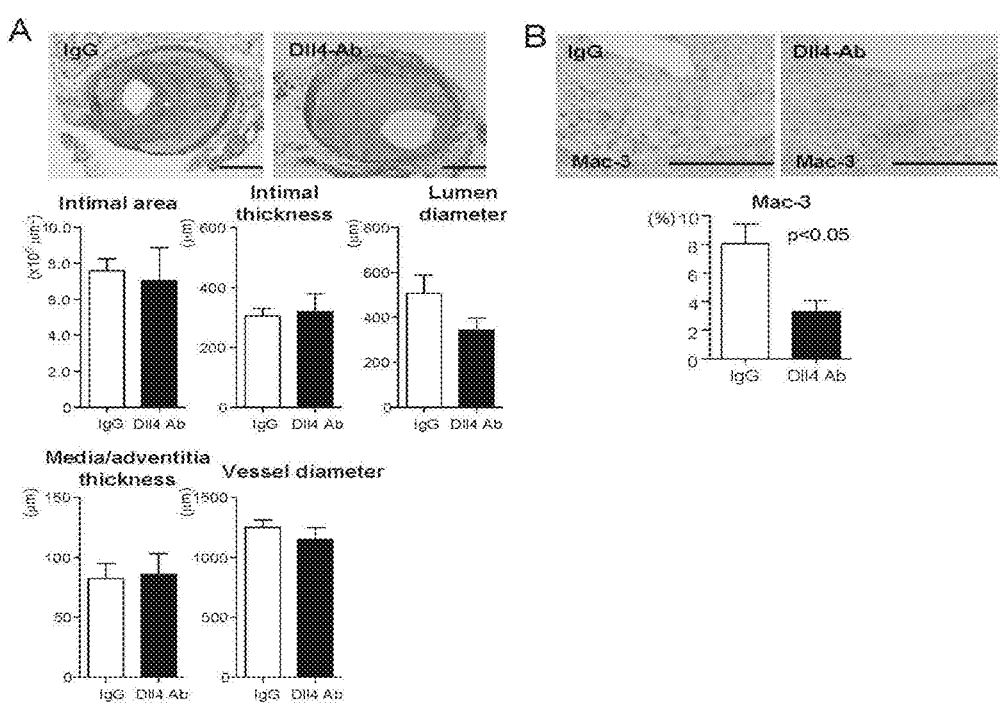
FIG. 13: 1-week administration of Dll4 antibody at the early phase reduced macrophage burden. (A) Dll4 blocking antibody or control IgG was administered until 7 days after vein graft implantation in high-fat-fed Ldlr−/− mice. Vein graft was harvested 28 days after implantation and stained by Masson-Trichrome staining. Scale bars indicate 400 μm. Bar graphs demonstrate the results of morphometric analyses. n=7 and 6. (B) Mac-3 staining of vein graft at Day 28. Macrophage accumulation was quantified as percentage of Mac-3-positive area in intimal layer. Scale bars indicate 200 μm. Bar graph shows the result of quantitative analysis. n=4 and 6.
Figure 14:
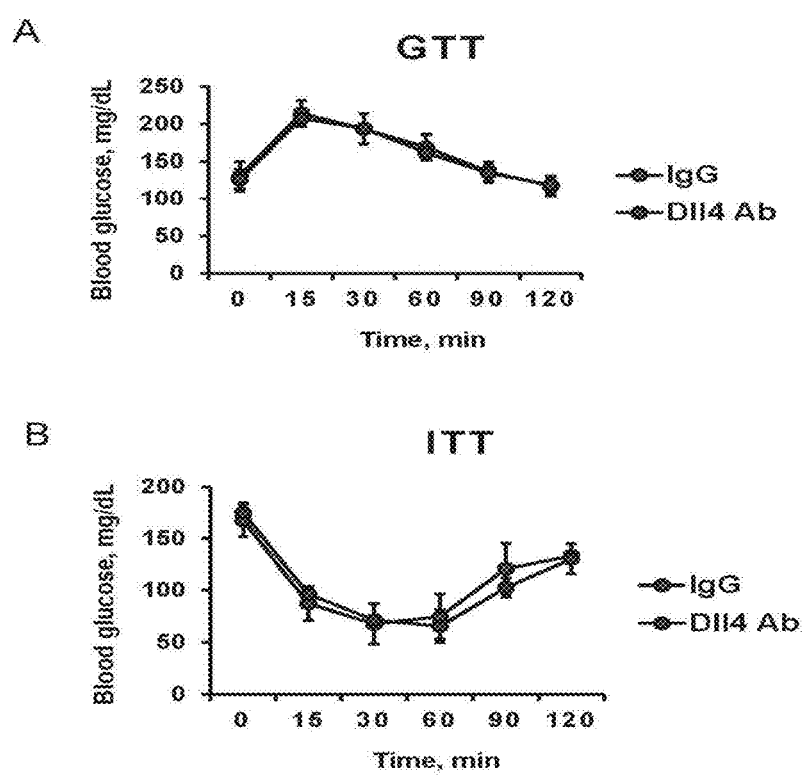
FIG. 14: Glucose metabolism and insulin sensitivity of Dll4 Ab treatment mice after day 7. (A) Ldlr−/− mice were treated with anti-Dll4 antibody (n=6) or control IgG (n=6) for 7 days and underwent (A) glucose tolerance test (GTT) and (B) Insulin tolerance test (ITT).

Dll4 antibody therapy for 7 days after graft implantation did not reduce lesion size at Day 28 (FIG. 13, panel A). It should be noted, however, that this short antibody administration produced a statistically significant reduction of macrophage accumulation, which was sustained until 21 days later (FIG. 13, panel B). We previously reported that Dll4 blockade for 12 weeks improves glucose tolerance and insulin sensitivity (Fukuda, et al., *Proc. Nat'l Acad. Sci. USA* 109:E1868-1877 (2012)). To address whether improved glucose metabolism may have contributed to the beneficial effects of Dll4 suppression on vein grafts, we examined glucose tolerance and insulin sensitivity 7 days after the initiation of antibody administration. Seven-day Dll4 antibody treatment caused no effects on these parameters (FIG. 14).

Figure 3:
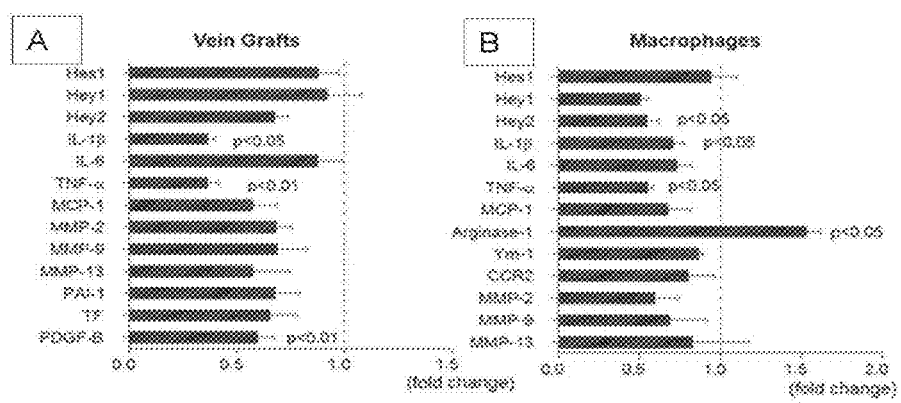
FIG. 3: mRNA in vein grafts (A) and F4/80 positive macrophages isolated from vein grafts. mRNA expression levels of molecules associated with inflammation, macrophage phenotype, matrix degradation, and thrombogenicity were quantified in vein grafts (A) and F4/80 positive macrophages isolated from vein grafts (B) 7 days after graft implantation. Data are represented as fold change by Dll4 antibody relative to control IgG PAI-1, plasminogen activator inhibitor-1; TF, tissue factor; CCR2, C—C chemokine receptor type 2. n=3 to 7.

Dll4 antibody-treated vein grafts contained lower levels of IL-10, TNF-α and PDGF-B mRNA compared to control grafts (FIG. 3, panel A). Using qPCR on macrophages isolated from vein grafts, we then examined whether the reduced expression of these factors merely resulted from a diminished macrophage number, or whether Dll4 blockade also reduced macrophage activation. Dll4 antibody treatment decreased macrophage expression of IL-1β and TNF-α, molecules typical of a pro-inflammatory "M1" phenotype (FIG. 3, panel B) (Moore, et al., *Nat. Rev. Immunol.* 13:709-721 (2013)). In contrast, Dll4 antibody therapy increased arginase 1 that represents non/anti-inflammatory "M2" polarization. A reduction of Hey2, a prototypical Notch target gene, indicates that Dll4 antibody indeed suppressed Notch signaling in macrophages. These results indicate that Dll4 suppression diminishes the pro-inflammatory microenvironment in vein grafts.

Dll4 Blockade Suppresses MMP Activity and Reduces Thin Collagen Fibers

Figure 4:
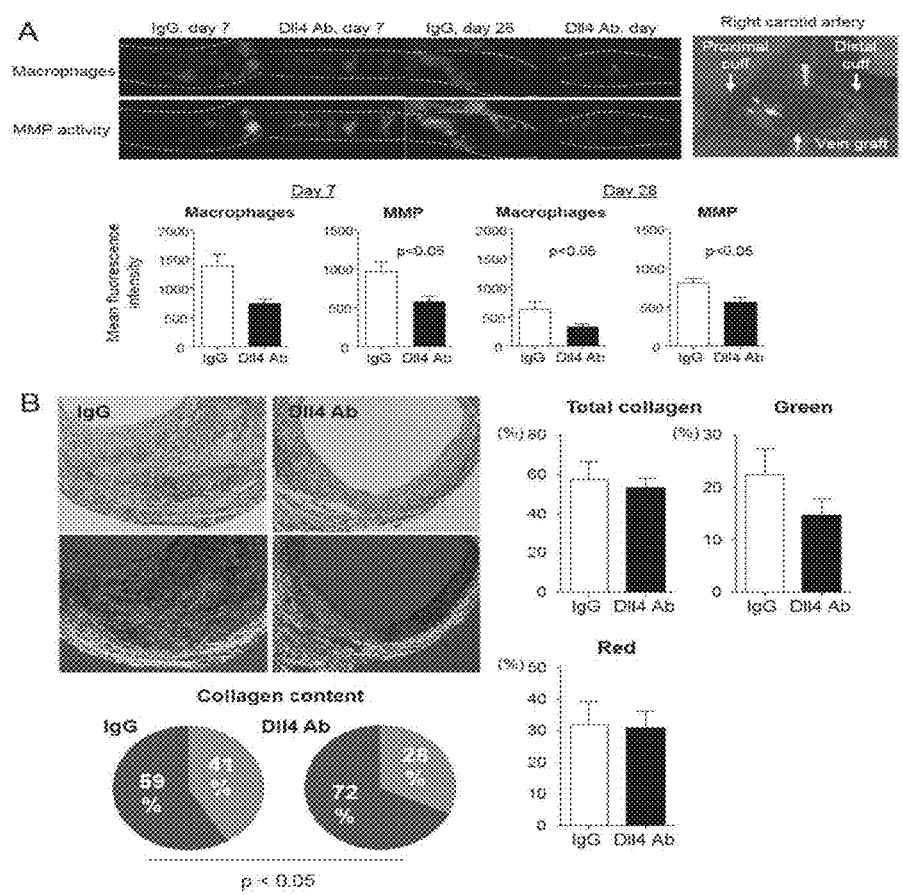
FIG. 4: Blockade of Dll4 inhibits MMP activity and collagen thinning. (A) Live molecular imaging of macrophage accumulation and MMP activity. Fluorescent probes (Aminospark 750 and MMPSense 680) were co-injected 24 hours before intravital microscopy. n=4 to 11. (B) Collagen content in the intima of vein grafts was quantified by picrosirius red staining under a polarized microscopy. Photomicrographs demonstrate representative samples without (top) or with (bottom) polarized light. Circle graphs indicate a ratio of green (thin) vs. red (thick) collagen fibers. n=6 and 5.

In vivo molecular imaging further assessed the effects of Dll4 suppression on macrophage activation in vein grafts. We co-injected two imaging agents that elaborate near-infrared signals to visualize macrophage phagocytic activity (750 nm) and MMP activity (680 nm). Dll4 blockade inhibited macrophage accumulation and MMP activity in parallel (FIG. 4, panel A). Picrosirius red staining viewed under a circularly polarized microscope showed no significant difference in the content of total fibrillar collagen between two groups (FIG. 4, panel B). Collagen hue analysis, however, revealed that Dll4 blockade decreased thin collagen fiber (FIG. 4, panel B), indicating that collagen degradation by macrophage-derived proteolytic activity may have reduced.

Figure 5:
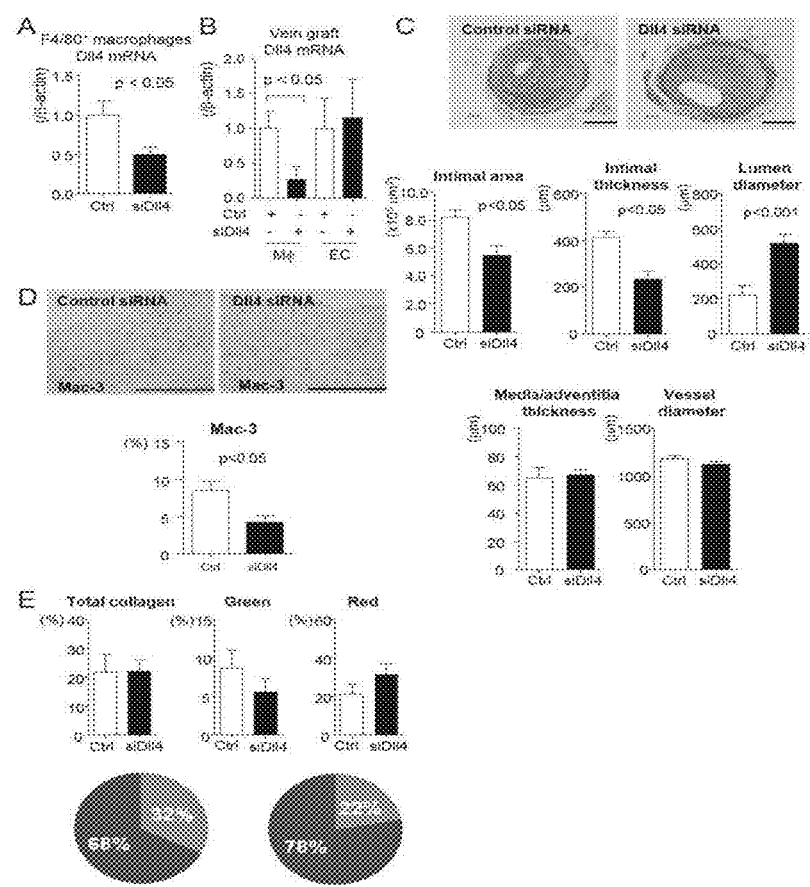
FIG. 5: The relative contribution of macrophage Dll4 in vein graft lesion development as examined via siRNA delivery to macrophages. (A) Macrophage-targeted lipid nanoparticles containing control siRNA (Ctrl) or Dll4 siRNA (siDll4) were injected via tail vein, and F4/80 positive splenic macrophages were isolated. Dll4 mRNA were quantified by real-time PCR. n=7. (B) Dll4 mRNA was quantified by real-time PCR in macrophages (Mφ) or endothelial cells (EC) collected by laser capture microdissection. n=5-6 sections. (C) Masson-Trichrome staining of vein grafts at day 28. Scale bars indicate 400 μm. n=9 and 8. (D) Mac-3 immunostaining at day 28. n=6. Scale bars indicate 200 μm. (E) Collagen analysis. Collagen content was analyzed 28 days after vein grafting by picrosirius red staining under a polarized microscope. Collagen hue analysis measured thin (green) and thick (red) collagen fibers. n=6 and 8.

Macrophage-Targeted Dll4 Silencing Inhibits Intimal Thickening and Macrophage Accumulation To determine the relative contribution of macrophage Dll4 to the development of vein graft lesions, we used macrophage-targeted LNP (C12-200) to deliver Dll4 siRNA in vivo (Novobrantseva, et al., *Mol. Ther. Nucleic Acids* 1:e4 (2012); Leuschner, et al., Nat. Biotechnol. 29:1005-1010 (2011)). In pilot experiments, a single injection of 0.5 mg/kg C12-200-siDll4 resulted in a 51% reduction of Dll4 mRNA in splenic macrophages in 72 hours (FIG. 5, panel A). To validate the selectivity to macrophages in vivo, we administered 0.5 mg/kg C12-200-siDll4 at 21 days and 24 days after vein graft implantation. qPCR after harvesting intimal tissues containing endothelium or macrophage clusters by laser capture microdissection showed inhibition of Dll4 expression in vein graft macrophages by >70%, but not in endothelium (FIG. 5, panel B).

C12-200-siDll4 was then injected at 0.5 mg/kg, twice a week, in Ldlr−/− mice. C12-200-siDll4 decreased intimal area and thickness as compared with control C12-200 containing non-targeting siRNA (FIG. 5, panel C). C12-200-siDll4 reduced macrophage accumulation in the intimal layer (FIG. 5, panel D), although it did not substantially increase thick collagen fibers (FIG. 5, panel E). These results indicate that Dll4 expressed by macrophages contributes to the lesion formation and macrophage burden in vein grafts.

Dll4 Regulates Expression of Pro-Inflammatory Molecules in Macrophages

Figure 6:
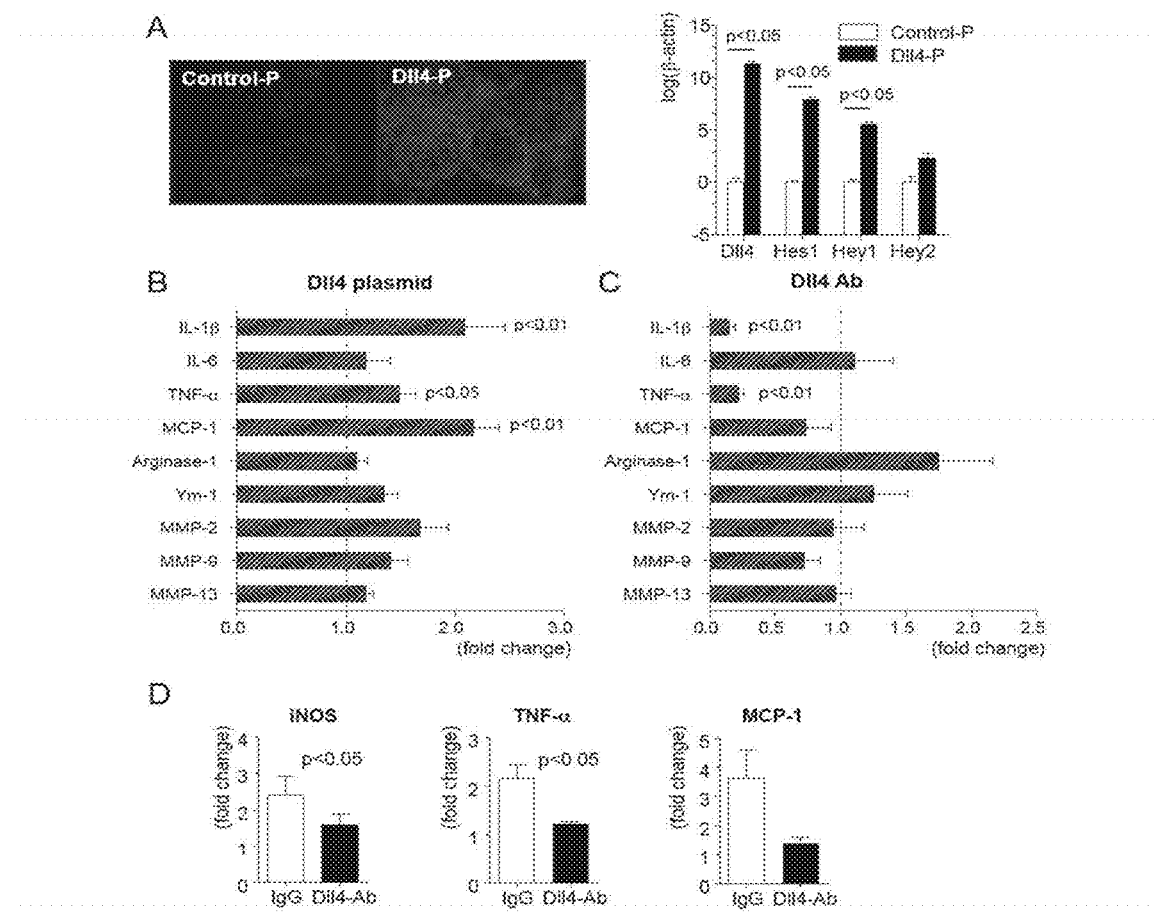
FIG. 6: In vitro gain-of-function and loss-of-function studies in primary macrophages. (A and B) A gain-of-function study. Immunofluorescence image of peritoneal macrophages 24 hours after control plasmid (Control-P) or Dll4 plasmid (Dll4-P) transfection (A). Bar graph shows quantitative analyses of Dll4 and prototypical Notch target genes (n=3) Data on the expression of molecules associated with vascular inflammation and remodeling are represented as fold change by Dll4 plasmid transfection relative to control plasmid transfection (n=6, B). (C) A loss-of-function study. Data are represented as fold change by Dll4 blocking antibody relative to control IgG n=5 and 6. (D) mRNA expression after IFNγ stimulation. Peritoneal macrophages were incubated overnight with control IgG or Dll4 antibody, and then stimulated with 10 ng/mL IFNγ for 4 hours. Bar graphs show results of real-time PCR. n=4.

To explore mechanistic evidence for the causal role of Dll4 in macrophage activation, we performed gain-of-function and loss-of-function experiments in mouse primary macrophages. Transient overexpression of Dll4 induced prototypical Notch target genes Hes1 and Hey1 (FIG. 6, panel A). Enforced expression of Dll4 induced and Dll4 blocking antibody suppressed pro-inflammatory molecules typical of "M1" macrophages (e.g., IL-1β, TNF-α; FIG. 6, panel B and 6, panel C). Dll4 blockade also inhibited IFN-γ-induced expression of pro-inflammatory genes iNOS and TNF-α (FIG. 6, panel D).

Macrophage Dll4 Promotes SMC Migration, Proliferation, and De-Differentiation

Figure 7:
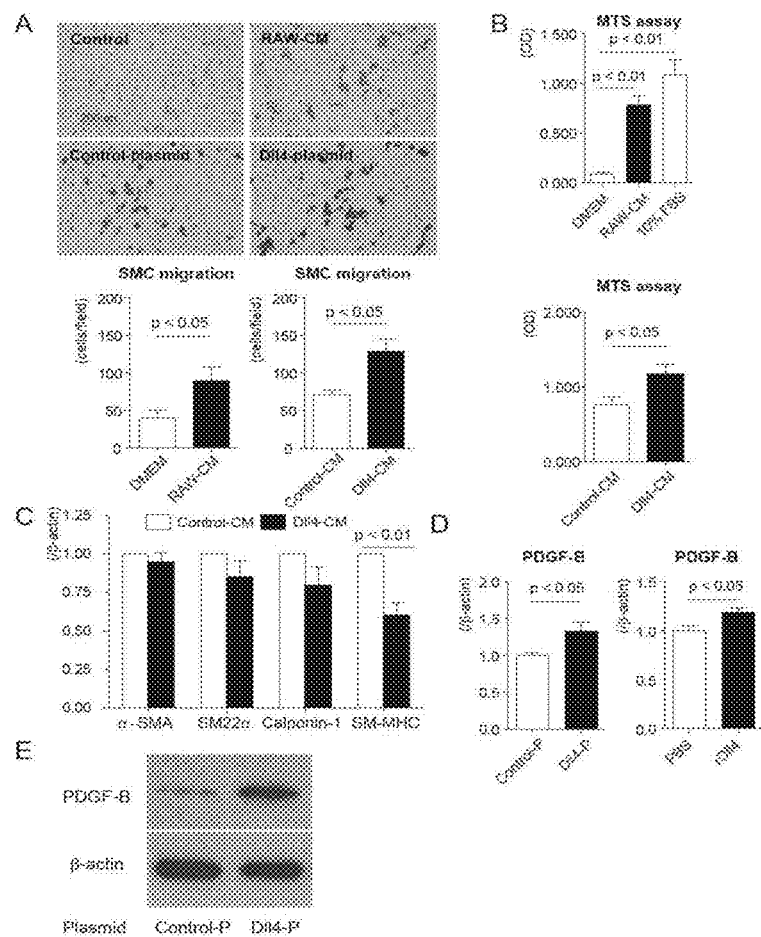
FIG. 7: Macrophage-SMC crosstalk as a possible mechanism of vein graft lesion development. (A) SMC migration was examined by modified Boyden's chamber method. DMEM, control Dulbecco's modified Eagle's medium; RAW-CM, conditioned media from non-treated RAW264.7 cells; Control-CM, CM from control plasmid transfected RAW264.7 cells; Dll4-CM, CM from Dll4 plasmid transfected RAW264.7 cells. n=4. (B) SMC proliferation induced by RAW-CM. RAW-CM increased SMC number compared with DMEM (above). Dll4-CM augmented CM-induced SMC growth (below). FBS; fetal bovine serum. n=8. (C) mRNA level of SMC differentiation markers after 24 hours of incubation with CM. Data are shown as relative expression normalized by SMCs treated with Control-CM. n=6. (D) mRNA expression levels of PDGF-B 24 hours after Dll4 plasmid transfection or immobilized Dll4 stimulation. Control-P, control plasmid; Dll4-P, Dll4 plasmid. n=6 (left) and n=7-8 (right). (E) Western blot of PDGF-B. Protein was extracted 24 hours after plasmid transfection.

SMC migration and proliferation may contribute to the development of vein graft lesions (Luscher, *Curr. Opin. Cardiol.* 6:868-876 (1991)). Notch signaling requires the direct cell-cell contact via the ligand-receptor binding. SMCs in the intima of atherosclerotic plaques and vein grafts are surrounded by extracellular matrix and generally lack membrane contacts with neighboring SMCs, while such direct contacts are common in plaque macrophages (Cox, et al., *Prog. Cardiovasc. Dis.* 34:45-68 (1991); Shimokama, et al., *Mod. Pathol.* 4:101-107 (1991); Vanderwal, et al., *Cardiovascular Pathology* 3:81-85 (1994)), suggesting that direct physical interactions between SMC and macrophages via Dll4-Notch binding may hardly occur. Therefore, we performed indirect co-culture experiments to examine whether macrophage expression of Dll4 induces SMC migration, proliferation, and de-differentiation by soluble factors. Conditioned media from RAW264.7 cells transfected with Dll4 plasmid accelerated SMC migration (FIG. 7, panel A), increased the SMC number (FIG. 7, panel B), and suppressed the expression of myosin heavy chain (SM-MHC), the most strict SMC differentiation marker (FIG. 7, panel C). PDGF-BB induces SMC migration, proliferation, and de-differentiation (Holycross, et al., *Circ. Res.* 71:1525-1532 (1992); Kenagy, et al., *J. Vasc. Surg.* 49:1282-1288 (2009)). Notch activation by enforced expression of Dll4 or immobilized recombinant Dll4 (rDll4) induced PDGF-B expression in RAW264.7 cells (FIG. 7, panels D and E), indicating that PDGF-BB may mediate the effects of Dll4 via macrophage-SMC crosstalk.

Figure 15:
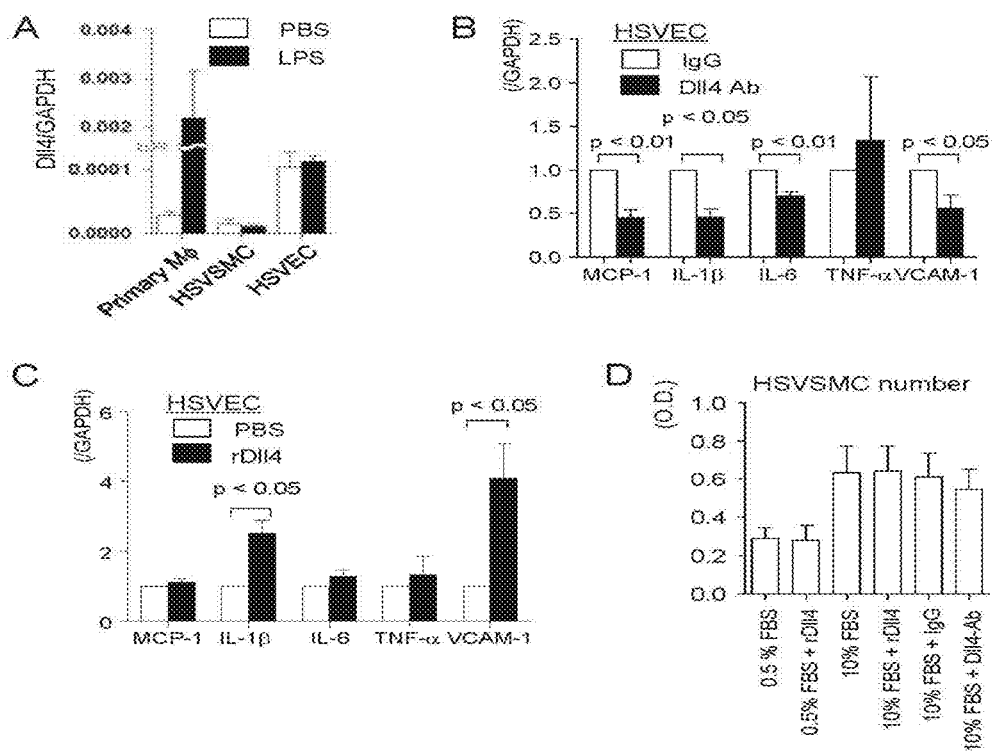
FIG. 15: The role of Dll4 on HSVSMCs and HSVECs. (A) Quantitative analyses of Dll4 mRNA levels with or without 3 hours of 10 ng/mL LPS stimulation. n=4-6. (B) HSVECs were incubated with 10 mg/mL of IgG or Dll4 blocking antibody. mRNA was extracted 24 hours later and quantified by real-time PCR. Data are shown as relative expression normalized by HSVECs treated with IgG n=5. (C) HSVECs were plated on immobilized Dll4, and RNA was extracted 24 hours later. Bar graph shows the results of real-time PCR. Data are shown as relative expression normalized by HSVECs treated with PBS. n=4 to 7. (D) HSVSMC number was measured by MTS assay. n=3.
Figure 16:
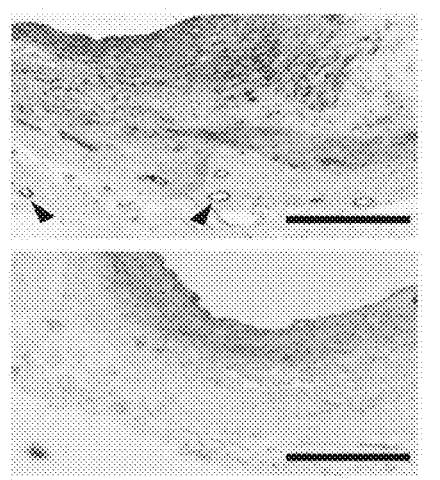
FIG. 16: Adventitial microvessels were quantified at 28 days after vein graft implantation. α-SMA positive luminal structures were considered as adventitial microvessels. Scale bar indicates 200 μm. N=6.
Figure 16:
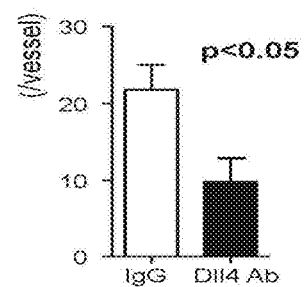
Figure 17:
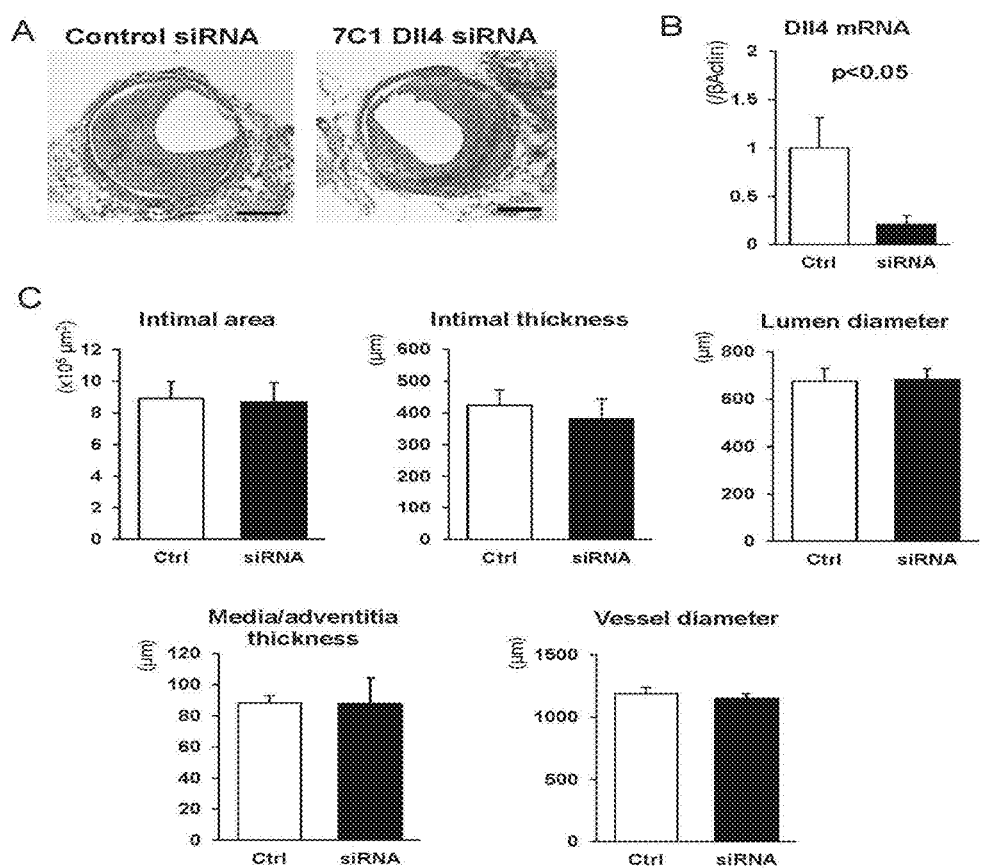
FIG. 17: The relative contribution of endothelial cell Dll4 in vein graft lesion development as examined via siRNA delivery to endothelium. Endothelial cell-targeted lipid nanoparticles (7C1) containing control siRNA (Ctrl) or Dll4 siRNA (siRNA) were injected via tail vein. (A) Masson-Trichrome stainings of vein grafts at day 28. Scale bars indicate 500 (B) Dll4 mRNA was quantified by real-time PCR in the endothelium (C) Bar graphs demonstrate the results of morphometric analysis (each n=6).

Dll4 Regulates Pro-Inflammatory Cytokine and Adhesion Molecule Expression in HSVECs Among human primary macrophages, human saphenous vein SMCs (HSVSMCs), and human saphenous vein endothelial cells (HSVECs), Dll4 mRNA levels were highest in HSVECs under the quiescent state (FIG. 15, panel A). LPS markedly induced Dll4 only in primary macrophages (FIG. 15, panel A). Endothelium also appeared positive for Dll4 in the failed human vein grafts (FIG. 1). In HSVECs, blockade of Dll4 suppressed MCP-1, IL-1β, IL-6, and VCAM-1 expression (FIG. 15, panel B), and immobilized Dll4 induced IL-1β and VCAM-1 mRNA expression (FIG. 15, panel C). Dll4 antibody treatment reduced the number of adventitial microvessels (FIG. 16). However, Dll4 silencing via endothelial cell (EC)-targeted LNP 7C1 (Dahlman, et al., *Nat. Nanotechnol.* 9:648-655 (2014)) produced no effects on the development of vein graft lesions (FIG. 17), further indicating the role of macrophage Dll4 in vein graft disease.

C. Discussion

Although many mechanisms have been proposed and validated for arterial diseases, the pathogenesis of vein graft disease remains obscure. Using two different biotherapies—blocking antibody and macrophage-targeted siRNA, the present study demonstrates a novel mechanism by which macrophage Dll4 promotes the development of vein graft lesions. Accumulating evidence has established that macrophages contribute to various mechanisms for arterial diseases, including plaque rupture (Libby, et al., *Nat. Med.* 8:1257-1262 (2002); Aikawa, et al., *Cardiovasc Pathol.* 13:125-138 (2004); Moore, et al., *Nat. Rev. Immunol.* 13:709-721 (2013)). The role of macrophages in vein graft disease, however, remains elusive. Failing vein grafts in patients exhibit macrophage accumulation (Cox, et al., *Prog. Cardiovasc. Dis.* 34:45-68 (1991)) and signs of rupture (Qiao, et al., *Am Heart J.* 122:955-958 (1991); Motwani, et al., *Circulation* 97: 916-931 (1998)). The present study demonstrates that accumulating macrophages in the neointima of failed human SVGs express Dll4, and that Dll4 expression increases during the development of experimental vein graft lesions. Clinical evidence has linked inflammation and vein graft failure (Owens, et al., *J. Vasc. Surg.* 45:2-9 (2007)). Preclinical studies proposed the role of macrophages in neointima formation in vein grafts (Eefting, et al., *J. Vasc. Surg.* 50:152-160 (2009); Tatewaki, et al., *J. Vasc. Surg.* 45:1236-1243 (2007); Jiang, et al., *FEBS Lett.* 583:3536-3540 (2009)). However, no medical therapies are currently available to target vein graft inflammation, which has driven our current efforts.

The key findings demonstrated in our study include: 1) the expression of Dll4 by macrophages in the intima of human and mouse vein grafts; 2) increased Dll4 expression and NICD accumulation during the development of experimental vein graft lesions; 3) positive correlations between the graft wall area and Dll4 expression or NICD accumulation; 4) reduced vein graft lesions after Dll4-targeted biotherapeutics (blocking antibody and macrophage-selective Dll4 siRNA); 5) the role of Dll4-Notch signaling in macrophage and SMC growth in vein grafts; 6) the effects of Dll4 blockade on macrophages being independent of metabolic effects; 7) the potential role of Dll4 in EC activation; 8) no substantial in vivo role for EC-derived Dll4 in vein graft disease as demonstrated by EC-targeted Dll4 siRNA; and 9) the role of Dll4-expressing macrophages in SMC de-differentiation, migration, and proliferation via a paracrine mechanism.

The emerging theory suggests macrophage polarization, often classified by at least two subpopulations: a pro-inflammatory ("M1") and an anti/non-inflammatory ("M2"), associated with various cardiovascular diseases (Moore, et al., *Nat. Rev. Immunol.* 13:709-721 (2013); Swirski, et al., *J. Clin. Invest.* 117:195-205 (2007)). In vein grafts, Dll4 blockade reduced the expression of multifunctional pro-inflammatory molecules IL-1β and TNF-α, suggesting the broad anti-atherogenic effects of Dll4 antibody via suppression of a positive feedback loop of sustained macrophage activation and providing insight into the clinical impact of this therapy. Examining the relative contribution of macrophage-derived Dll4 used the macrophage-targeted LNP C12-200 and EC-targeted LNP 7C1. Dll4 silencing via C12-200 decreased macrophage accumulation and intimal thickening, while Dll4 siRNA in 7C1 produced no changes, providing compelling evidence for the role of macrophage Dll4 in the development of inflamed vein grafts.

Because SMC may also participate in the pathogenesis of vein graft disease (Luscher, *Curr. Opin. Cardiol.* 6:868-876 (1991)), we explored the novel mechanism that Dll4 promotes SMC activation. Dll4 expression levels were, however, much lower in primary SMCs than those in macrophages (FIG. 15, panel A). Previous studies demonstrate a lack of membrane contact between SMCs surrounded by extracellular matrix, while direct contact between macrophages is common (Shimokama, et al., *Mod. Pathol.* 4:101-107 (1991); Vanderwal, et al., *Cardiovascular Pathology* 3:81-85 (1994)). Notch signaling activation requires direct cell-to-cell contact that allows ligand-receptor binding. Thus, Dll4-Notch interaction between neighboring SMCs or between SMCs and macrophages may not occur so frequently in vascular lesions. Our evidence suggests a paracrine mechanism by which macrophage Dll4 activates neighboring SMCs.

To maximize therapeutic relevance of our study, we used two scientifically validated and clinically relevant techniques to suppress Dll4. LNP-mediated RNAi, a robust and well-established tool for investigating the role of macrophage gene expression in vivo, enabled us to selectively silence Dll4 in macrophages. As documented in the previous and present studies, the LNP C12-200 helps to reduce the macrophage expression of a gene of interest (Novobrantseva, et al., *Mol. Ther. Nucleic Acids* 1:e4 (2012); Leuschner, et al., *Nat. Biotechnol.* 29:1005-1010 (2011); Courties, et al., *J. Am. Coll. Cardiol.* 63:1556-1566 (2014); Leuschner, et al., *Eur Heart J.* pg 1-12 (Jun. 20, 2014)). It should be noted that the delivery of siRNA in LNP has generated promising clinical data (Fitzgerald, et al., *Lancet* 383:60-68 (2014); Kanasty, et al., *Nat. Mater.* 12:967-977 (2013); Coelho, et al., *N. Engl. J. Med.* 369:819-829 (2013)). In addition, antibody therapies for chronic diseases have become available in the clinic. An ongoing cardiovascular outcome trial on anti-IL-1β antibody has presented anti-inflammatory effects (Ridker, et al., *Circulation* 126:2739-2748 (2012)). These lines of evidence suggest the clinical translatability of our data.

Figure 18:
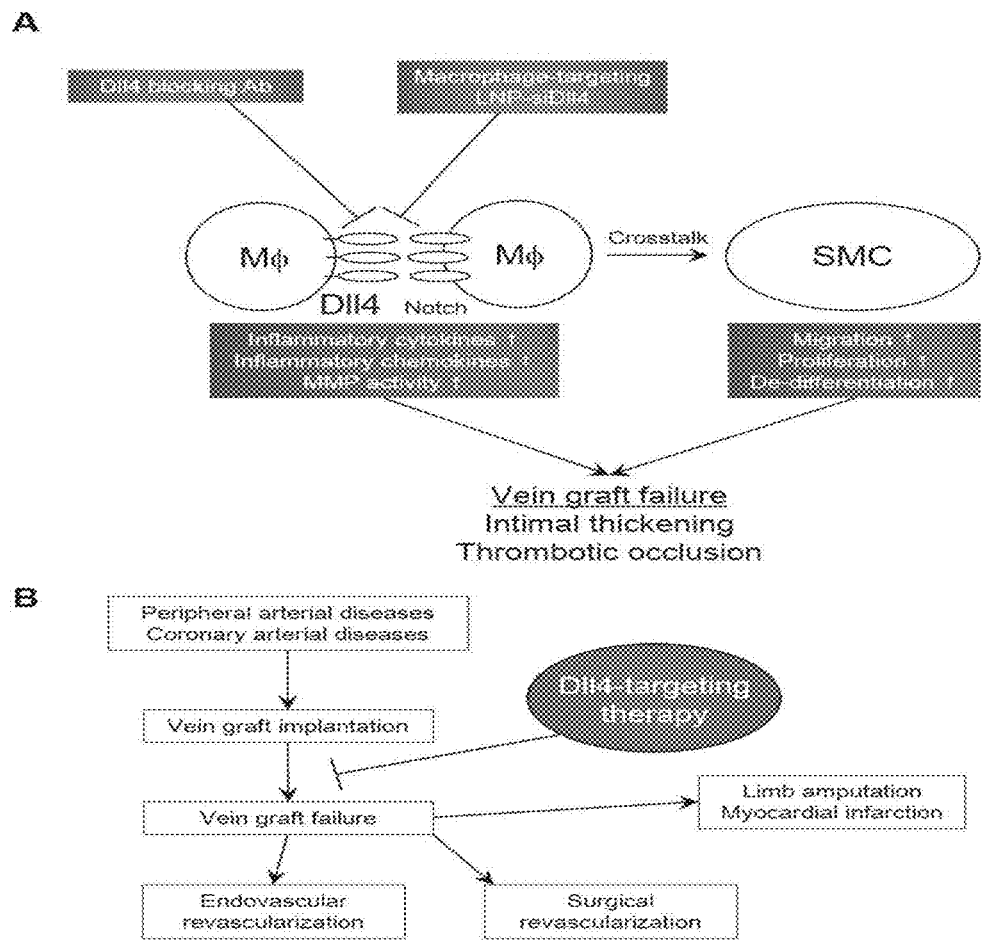
FIG. 18: Schematic views summarizing key novel findings and clinical perspectives. (A) Macrophage Dll4-Notch signaling as a key player of vein graft lesion development. Dll4 activates lesional macrophages, which can form a positive feedback loop of inflammation. Crosstalk between Dll4-Notch-activated macrophages and SMCs may modulate SMC phenotype and promote lesion development. Dll4 blocking antibody or macrophage-targeted Dll4 siRNA inhibits Dll4-mediated vascular inflammation and remodeling. SMC, smooth muscle cells; Mϕ, macrophages. (B) Clinical perspectives. Dll4-targeted biotherapies (blocking antibody and macrophage-targeted siRNA) may serve as possible therapeutic options for the prevention of vein graft failure.

In conclusion, evidence has been provided that the Dll4-Notch axis in macrophages contributes to the pathogenesis of vein graft lesion development (FIG. 18, panel A). The study has identified Dll4 as a new promising therapeutic target for vein graft failure (FIG. 18, panel B), a major clinical problem with no medical solutions.

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of treating a patient to reduce the risk of vein graft failure, comprising administering to said patient a therapeutically effective amount of a compound selected from the group consisting of: an anti-Delta-like 4 antibody and a Delta-like 4 (Dll4) siRNA, wherein said compound inhibits a Notch signaling pathway.

2. The method of claim 1, wherein said compound inhibits a Notch signaling pathway in macrophages.

3. The method of claim 1, wherein said compound blocks the binding of Dll4 to Notch receptors.

4. The method of claim 3, wherein said Notch receptor(s) are/is of the Notch1 or Notch3 receptor subtype(s).

5. The method of claim 1, wherein said vein graft is an autologous saphenous vein graft.

6. The method of claim 1, wherein said patient has received said vein graft as a treatment for peripheral artery disease or during coronary bypass surgery.

7. The method of claim 1, wherein said compound is administered orally as a capsule, tablet or pill or systemically by injection.

8. The method of claim 1, wherein said compound is administered locally by injection, by infusing said vein graft with said compound before implantation in said patient, and/or by implanting in close proximity to said vein graft a gel or other matrix that slowly releases said compound.

9. The method of claim 1, wherein said compound is administered to said patient in a pharmaceutical composition comprising the compound along with a pharmaceutically acceptable carrier.

10. The method of claim 1, wherein said compound is an anti-Delta-like 4 antibody that blocks the binding of Dll4 to a Notch receptor.

11. The method of claim 10, wherein said vein graft is an autologous saphenous vein graft.

12. The method of claim 10, wherein said patient has received said vein graft as a treatment for peripheral artery disease or during coronary bypass surgery.

13. The method of claim 10, wherein said compound is administered locally by injection, by infusing said vein graft with said compound before implantation in said patient, and/or by implanting in close proximity to said vein graft a gel or other matrix that slowly releases said compound.

14. The method of claim 1, wherein said compound is a Dll4 siRNA.

15. The method of claim 14, wherein said patient has received said vein graft as a treatment for peripheral artery disease or during coronary bypass surgery.

16. The method of claim 14, wherein said compound is administered systemically and is in a pharmaceutical composition comprising the compound along with a pharmaceutically acceptable carrier.

17. The method of claim 14, wherein said compound is administered locally by injection, by infusing said vein graft with said compound before implantation in said patient, and/or by implanting in close proximity to said vein graft a gel or other matrix that slowly releases said compound.

18. A method of treating a patient subsequent to the implantation of a vein graft, comprising administering to said patient a compound selected from the group consisting of: an anti-Delta-like 4 antibody and a Delta-like 4 (Dll4) siRNA, wherein said compound is administered at a dose of 0.01 to 500 mg/kg and inhibits a Notch signaling pathway.

19. The method of claim 18, wherein said patient has received said vein graft as a treatment for peripheral artery disease or during coronary bypass surgery.

20. The method of claim 18, wherein said compound is administered locally by injection, by infusing said vein graft with said compound before implantation in said patient, and/or by implanting in close proximity to said vein graft a gel or other matrix that slowly releases said compound.

* * * * *

UNITED STATES PATENT AND TRADEMARK OFFICE
CERTIFICATE OF CORRECTION

PATENT NO. : 9,567,396 B2
APPLICATION NO. : 14/855380
DATED : February 14, 2017
INVENTOR(S) : Masanori Aikawa et al.

It is certified that error appears in the above-identified patent and that said Letters Patent is hereby corrected as shown below:

On the Title Page

In item (73), the only assignee named should be The Brigham and Women's Hospital, Inc.

In item (60), the information regarding related applications should read:

Continuation-in-part of application No. 13/903,288, filed on May 28, 2013, now Pat. No. 9,289,489, which is a continuation of application No. 13/358,425, filed on Jan. 25, 2012, now abandoned, which is a continuation of application No. 12/230,867, filed as application No. PCT/US2007/005267 on Mar. 2, 2007, now Pat. No. US 8,133,857.

Continuation-in-part of US 14/508,994, filed on Oct. 7, 2014, which is a division of application No. 13/461,365, filed on May 1, 2012, now Pat. No. 8,889,131, which is a continuation-in-part of application No. PCT/US2010/054798, filed on Oct. 29, 2010.

Provisional application No. 60/779,445, filed on Mar. 7, 2006, provisional application No. 61/257,026, filed on Nov. 1, 2009.

Signed and Sealed this
Thirtieth Day of May, 2017

Michelle K. Lee
*Director of the United States Patent and Trademark Office*

SEQUENCE LISTING

```
<160> NUMBER OF SEQ ID NOS: 44

<210> SEQ ID NO 1
<211> LENGTH: 22
<212> TYPE: DNA
<213> ORGANISM: Mus musculus

<400> SEQUENCE: 1
cctgagcgca agtactctgt gt                                          22

<210> SEQ ID NO 2
<211> LENGTH: 21
<212> TYPE: DNA
<213> ORGANISM: Mus musculus

<400> SEQUENCE: 2
gctgatccac atctgctgga a                                           21

<210> SEQ ID NO 3
<211> LENGTH: 20
<212> TYPE: DNA
<213> ORGANISM: Mus musculus

<400> SEQUENCE: 3
acctttggca atgtctccac                                             20

<210> SEQ ID NO 4
<211> LENGTH: 20
<212> TYPE: DNA
<213> ORGANISM: Mus musculus

<400> SEQUENCE: 4
gtttcctggc gaagtctctg                                             20

<210> SEQ ID NO 5
<211> LENGTH: 20
<212> TYPE: DNA
<213> ORGANISM: Mus musculus

<400> SEQUENCE: 5
```
acaccggaca aaccaaagac                                              20

<210> SEQ ID NO 6
<211> LENGTH: 20
<212> TYPE: DNA
<213> ORGANISM: Mus musculus

<400> SEQUENCE: 6
atgccgggag ctatctttct                                              20

<210> SEQ ID NO 7
<211> LENGTH: 20
<212> TYPE: DNA
<213> ORGANISM: Mus musculus

<400> SEQUENCE: 7
ggtacccagt gcctttgaga                                              20

<210> SEQ ID NO 8
<211> LENGTH: 20
<212> TYPE: DNA
<213> ORGANISM: Mus musculus

<400> SEQUENCE: 8
atgctcagat aacgggcaac                                              20

<210> SEQ ID NO 9
<211> LENGTH: 20
<212> TYPE: DNA
<213> ORGANISM: Mus musculus

<400> SEQUENCE: 9
gttccgctag gcgacagtag                                              20

<210> SEQ ID NO 10
<211> LENGTH: 20
<212> TYPE: DNA
<213> ORGANISM: Mus musculus

<400> SEQUENCE: 10
tgcccagggt aattgttctc                                              20

<210> SEQ ID NO 11
<211> LENGTH: 20
<212> TYPE: DNA
<213> ORGANISM: Mus musculus

<400> SEQUENCE: 11
gcccatcctc tgtgactcat                                              20

<210> SEQ ID NO 12
<211> LENGTH: 20
<212> TYPE: DNA
<213> ORGANISM: Mus musculus

<400> SEQUENCE: 12
aggccacagg tattttgtcg                                              20

<210> SEQ ID NO 13
<211> LENGTH: 20
<212> TYPE: DNA
<213> ORGANISM: Mus musculus

<400> SEQUENCE: 13
agttgccttc ttgggactga                                               20

<210> SEQ ID NO 14
<211> LENGTH: 20
<212> TYPE: DNA
<213> ORGANISM: Mus musculus

<400> SEQUENCE: 14
tccacgattt cccagagaac                                               20

<210> SEQ ID NO 15
<211> LENGTH: 20
<212> TYPE: DNA
<213> ORGANISM: Mus musculus

<400> SEQUENCE: 15
agcccccagt ctgtatcctt                                               20

<210> SEQ ID NO 16
<211> LENGTH: 20
<212> TYPE: DNA
<213> ORGANISM: Mus musculus

<400> SEQUENCE: 16
ctccctttgc agaactcagg                                               20

<210> SEQ ID NO 17
<211> LENGTH: 20
<212> TYPE: DNA
<213> ORGANISM: Mus musculus

<400> SEQUENCE: 17
aggtccctgt catgcttctg                                               20

<210> SEQ ID NO 18
<211> LENGTH: 20
<212> TYPE: DNA
<213> ORGANISM: Mus musculus

<400> SEQUENCE: 18
tctggaccca ttccttcttg                                               20

<210> SEQ ID NO 19
<211> LENGTH: 21
<212> TYPE: DNA
<213> ORGANISM: Mus musculus

<400> SEQUENCE: 19
ccccatgaag ccttgtttac c                                             21

<210> SEQ ID NO 20
<211> LENGTH: 20
<212> TYPE: DNA
<213> ORGANISM: Mus musculus

<400> SEQUENCE: 20
ttgtaggagg tgccctggaa                                               20

<210> SEQ ID NO 21
<211> LENGTH: 20
<212> TYPE: DNA
<213> ORGANISM: Mus musculus

```
<400> SEQUENCE: 21
gaaggcaaac cctgtgtgtt                                              20

<210> SEQ ID NO 22
<211> LENGTH: 20
<212> TYPE: DNA
<213> ORGANISM: Mus musculus

<400> SEQUENCE: 22
agagtactgc ttgcccagga                                              20

<210> SEQ ID NO 23
<211> LENGTH: 20
<212> TYPE: DNA
<213> ORGANISM: Mus musculus

<400> SEQUENCE: 23
gagccacaga tgagcacaga                                              20

<210> SEQ ID NO 24
<211> LENGTH: 20
<212> TYPE: DNA
<213> ORGANISM: Mus musculus

<400> SEQUENCE: 24
atgtaaggcc acctccactg                                              20

<210> SEQ ID NO 25
<211> LENGTH: 20
<212> TYPE: DNA
<213> ORGANISM: Mus musculus

<400> SEQUENCE: 25
acgttgtgga actgccctac                                              20

<210> SEQ ID NO 26
<211> LENGTH: 20
<212> TYPE: DNA
<213> ORGANISM: Mus musculus

<400> SEQUENCE: 26
gccagggttg cactaaacat                                              20

<210> SEQ ID NO 27
<211> LENGTH: 20
<212> TYPE: DNA
<213> ORGANISM: Mus musculus

<400> SEQUENCE: 27
tcctggccac catctttatc                                              20

<210> SEQ ID NO 28
<211> LENGTH: 20
<212> TYPE: DNA
<213> ORGANISM: Mus musculus

<400> SEQUENCE: 28
atgttgcaca gttcccatca                                              20

<210> SEQ ID NO 29
<211> LENGTH: 20
<212> TYPE: DNA
```

```
<213> ORGANISM: Mus musculus

<400> SEQUENCE: 29
acgttgtgga actgccctac                                              20

<210> SEQ ID NO 30
<211> LENGTH: 20
<212> TYPE: DNA
<213> ORGANISM: Mus musculus

<400> SEQUENCE: 30
gccagggttg cactaaacat                                              20

<210> SEQ ID NO 31
<211> LENGTH: 20
<212> TYPE: DNA
<213> ORGANISM: Mus musculus

<400> SEQUENCE: 31
tcacctgagc tttgatgtcg                                              20

<210> SEQ ID NO 32
<211> LENGTH: 20
<212> TYPE: DNA
<213> ORGANISM: Mus musculus

<400> SEQUENCE: 32
cacctcctct gctgtcttcc                                              20

<210> SEQ ID NO 33
<211> LENGTH: 20
<212> TYPE: DNA
<213> ORGANISM: Mus musculus

<400> SEQUENCE: 33
gaaggagcca ctgaggtctg                                              20

<210> SEQ ID NO 34
<211> LENGTH: 20
<212> TYPE: DNA
<213> ORGANISM: Mus musculus

<400> SEQUENCE: 34
cacggcacct cctaaattgt                                              20

<210> SEQ ID NO 35
<211> LENGTH: 20
<212> TYPE: DNA
<213> ORGANISM: Mus musculus

<400> SEQUENCE: 35
cctgcaaaga ccagaagagg                                              20

<210> SEQ ID NO 36
<211> LENGTH: 20
<212> TYPE: DNA
<213> ORGANISM: Mus musculus

<400> SEQUENCE: 36
tatgccgtgg atgaactgag                                              20

<210> SEQ ID NO 37
<211> LENGTH: 20
```

```
<212> TYPE: DNA
<213> ORGANISM: Mus musculus

<400> SEQUENCE: 37
cttcgctggt gatgatgctc                                                20

<210> SEQ ID NO 38
<211> LENGTH: 20
<212> TYPE: DNA
<213> ORGANISM: Mus musculus

<400> SEQUENCE: 38
ttggtgatga tgccgtgttc                                                20

<210> SEQ ID NO 39
<211> LENGTH: 20
<212> TYPE: DNA
<213> ORGANISM: Mus musculus

<400> SEQUENCE: 39
caagccttct ctgcctcaac                                                20

<210> SEQ ID NO 40
<211> LENGTH: 20
<212> TYPE: DNA
<213> ORGANISM: Mus musculus

<400> SEQUENCE: 40
tcgatccctc aggatacagg                                                20

<210> SEQ ID NO 41
<211> LENGTH: 20
<212> TYPE: DNA
<213> ORGANISM: Mus musculus

<400> SEQUENCE: 41
ggggacactt agacccttga                                                20

<210> SEQ ID NO 42
<211> LENGTH: 20
<212> TYPE: DNA
<213> ORGANISM: Mus musculus

<400> SEQUENCE: 42
gccatacctg cagtccaatg                                                20

<210> SEQ ID NO 43
<211> LENGTH: 20
<212> TYPE: DNA
<213> ORGANISM: Mus musculus

<400> SEQUENCE: 43
gtctccagca caaatgctca                                                20

<210> SEQ ID NO 44
<211> LENGTH: 20
<212> TYPE: DNA
<213> ORGANISM: Mus musculus

<400> SEQUENCE: 44
agtacacgtc aggggcaatc                                                20
```